(12) United States Patent
Buggy et al.

(10) Patent No.: US 7,820,711 B2
(45) Date of Patent: Oct. 26, 2010

(54) USES OF SELECTIVE INHIBITORS OF HDAC8 FOR TREATMENT OF T-CELL PROLIFERATIVE DISORDERS

(75) Inventors: Joseph J. Buggy, Mountain View, CA (US); Sriram Balasubramanian, San Carlos, CA (US)

(73) Assignee: Pharmacyclics Inc., Sunnyvale, CA (US)

( * ) Notice: Subject to any disclaimer, the term of this patent is extended or adjusted under 35 U.S.C. 154(b) by 694 days.

(21) Appl. No.: 11/779,743

(22) Filed: Jul. 18, 2007

(65) Prior Publication Data

US 2008/0112889 A1 May 15, 2008

Related U.S. Application Data

(60) Provisional application No. 60/865,825, filed on Nov. 14, 2006, provisional application No. 60/911,857, filed on Apr. 13, 2007, provisional application No. 60/944,409, filed on Jun. 15, 2007.

(51) Int. Cl.
*A61K 31/40* (2006.01)

(52) U.S. Cl. .................. 514/412; 514/414; 514/416

(58) Field of Classification Search ................. 514/412, 514/414, 416
See application file for complete search history.

(56) References Cited

U.S. PATENT DOCUMENTS

| | | | |
|---|---|---|---|
| 6,358,992 B1 | 3/2002 | Pamukcu et al. | |
| 6,875,598 B1 | 4/2005 | Buggy et al. | |
| 7,220,774 B2 | 5/2007 | Albert | |
| 2004/0157930 A1 | 8/2004 | Mascagni | |
| 2005/0080249 A1 | 4/2005 | Buggy | |

| | | | |
|---|---|---|---|
| 2007/0281934 A1 | 12/2007 | Buggy et al. | |

FOREIGN PATENT DOCUMENTS

| | | | |
|---|---|---|---|
| WO | WO-2004-061101 A1 | 7/2004 | |
| WO | WO-2004-089293 A2 | 10/2004 | |
| WO | WO-2004-110418 A2 | 12/2004 | |

OTHER PUBLICATIONS

Laport, G. G. et al., "Adoptive transfer of costimulated T cells induces lymphocytosis in patients with relapsed/refractory non-Hodgkin lymphoma following CD34+-selected hematopoietic cell transplantation," Blood 102(6):2004-2013 (2003).
Porter et al., "A phase 1 trial of donor lymphocyte infusions expanded and activated ex vivo via CD3/CD28 costimulation," Blood 107(4):1325-1331 (2006).
Rapoport, A.P. et al., "Restoration of immunity in lymphopenic individuals with cancer by vaccination and adoptive T-cell transfer," Nat. Med. 11(11):1230-1237 (2005).
Schultz, B.E. et al., "Kinetics and Comparative Reactivity of Human Class I and Class IIb Histone Deacetylases," Biochemistry 43(34):11083-11091 (2004).
Somoza, J.R. et al., "Structural Snapshots of Human HDAC8 Provide Insights Into the Class I Histone Deacetylases," Structure 12(7):1325-1334 (2004).
Won, J. and Kim, T.K., "Histone Modifications and Transcription Factor Binding on Chromatin: ChIP-PCR Assays," Methods Mol. Biol. 325:273-283 (2006).
PCT/US07/73802 Search Report dated Mar. 20, 2008.
PCT/US07/84718 Search Report dated Mar. 31, 2008.

*Primary Examiner*—Raymond J Henley, III
(74) *Attorney, Agent, or Firm*—Wilson Sonsini Goodrich & Rosati

(57) ABSTRACT

Described herein are methods for treating a subject suffering from a T-cell lymphoma by administering to the subject a pharmaceutical composition containing a therapeutically effective amount of a selective inhibitor of histone deacetylase 8. Also described herein are methods for treating a subject suffering from a T-cell lymphoma by administering to the subject a population of autologous T-cells that have been exposed to a selective HDAC8 inhibitor composition ex vivo.

27 Claims, 15 Drawing Sheets

HDAC8 protein is found in tumor cell lines

HDAC8 knockdown leads to apoptosis

Compound 23 does not inhibit growth of selected solid tumor lines

*H33HJ-JA1, OVCAR-3, MIA PaCa-2, PANC-1*

Compound 23 does not inhibit growth of HCT116 or human PBMCs

Compound 23 is cytotoxic to T-cell derived tumor cells

- Cytotoxic
  - T-cell derived cell lines
    - Jurkat ($GI_{50}$ = 3 µM)
    - HuT78 ($GI_{50}$ = 4 µM)

- Not cytotoxic
  - B-cell derived cell lines
    - DB ($GI_{50}$ >20 µM)
    - K562 ($GI_{50}$ >20 µM)
  - 8/8 Solid tumor lines
  - Human normal PBMCs (24 hrs)

Fig. 8
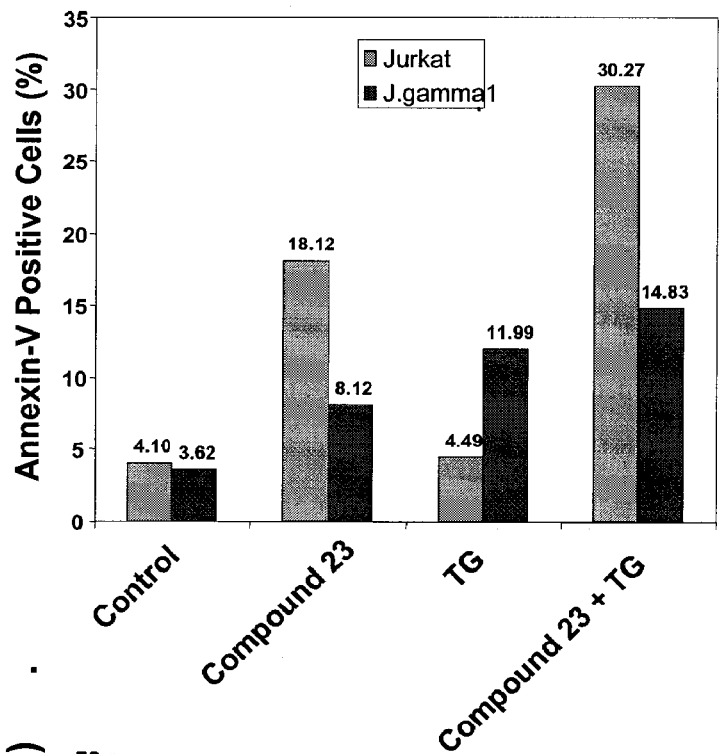
A
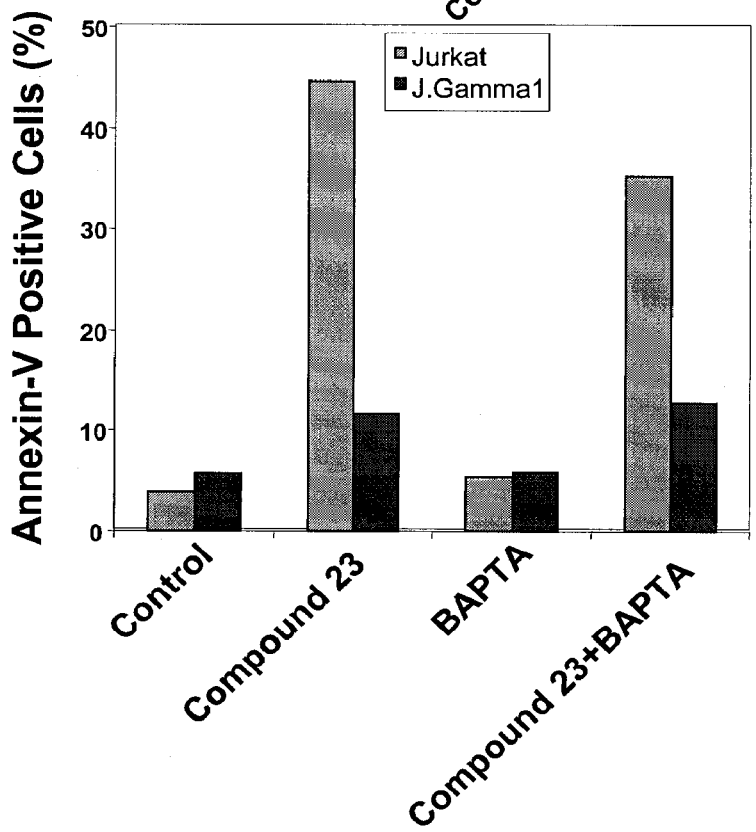
B

Calcium Mobilization
Jurkat Cells treated with Compound A: Dose Titration

US 7,820,711 B2

USES OF SELECTIVE INHIBITORS OF HDAC8 FOR TREATMENT OF T-CELL PROLIFERATIVE DISORDERS

RELATED APPLICATIONS

This application claims the benefit of U.S. Provisional Patent Application No. 60/865,825 filed Nov. 14, 2006, U.S. Provisional Patent Application No. 60/911,857 filed Apr. 13, 2007, and U.S. Provisional Patent Application No. 60/944,409 filed Jun. 15, 2007; the disclosures of these references are herein incorporated in their entirety.

BACKGROUND

Histone deacetylases (HDACs) catalyze the removal of acetyl groups from histones, proteins that organize and modulate the structure of chromatin in nucleosomes. HDAC-mediated deacetylation of chromatin-bound histones regulates the expression of a variety of genes throughout the genome. Importantly, HDACs have been linked to cancer. To date, eleven major HDAC isoforms have been described (HDACs 1-11). Certain HDACs are overexpressed in, e.g., prostate cancer (HDAC1), colon cancers (HDAC3), and breast cancers (HDAC6). Indeed, HDAC activity is increasingly recognized as playing an important role in the onset and progression of cancer, as well as other health conditions.

SUMMARY OF THE INVENTION

Described herein are methods and compositions for treating T-cell proliferative disorders in which the treatment or composition includes a selective inhibitor of histone deacetylase 8 (abbreviated as HDAC8). Also described herein are methods for determining whether a particular T-cell proliferative disorder could be treated using a selective inhibitor of HDAC8. Also described herein are methods for assessing and/or predicting the effectiveness of a particular HDAC8 inhibitor (including the dose levels and/or dose schedules) for or in the treatment of a T-cell proliferative disorder.

In one aspect are methods for treating a T-cell proliferative disorder, comprising administering to a subject in need a composition containing a therapeutically effective amount of a selective inhibitor of histone deacetylase 8 activity.

In one embodiment of such methods, the selective inhibitor is a compound of formula Ia or IIa:

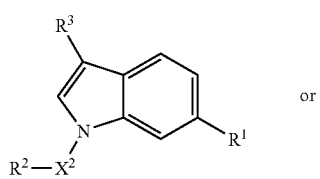

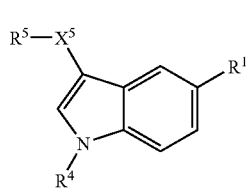

where
$R^1$ in Formula Ia or IIa is —C(O)NHOH;
$X^2$ is a bond, alkylene, or alkenylene where the alkylene or alkenylene is optionally substituted with one, two, three, four, or five halo;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
$R^3$ is hydrogen, alkyl, substituted alkyl, alkenyl, substituted alkenyl, hydroxy, alkoxy, or haloalkoxy;
$R^4$ is hydrogen, alkyl, substituted alkyl, alkenyl, substituted alkenyl, hydroxy, alkoxy, haloalkoxy, or optionally substituted phenyl;
$X^5$ is a bond, alkylene, or alkenylene where the alkylene or alkenylene is optionally substituted with halo; and
$R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In another embodiment of such methods, the selective inhibitor is a compound of Formula Ib or IIb:

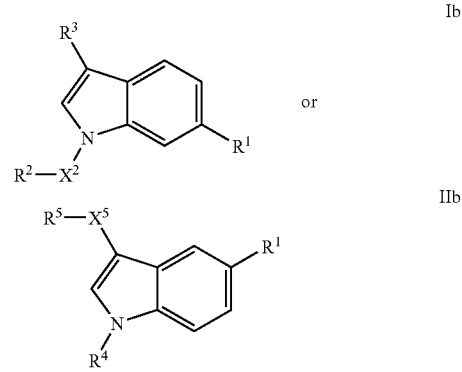

where
$R^1$ in Formula Ib or IIb is —C(O)NHOH;
$X^2$ is a bond, alkylene, or alkenylene where the alkylene or alkenylene is optionally substituted with one, two, three, four, or five halo;
$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);

$R^4$ is hydrogen, alkyl, substituted alkyl, alkenyl, substituted alkenyl, hydroxy, alkoxy, haloalkoxy, or optionally substituted phenyl; and $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the composition further comprises an agent that activates phospholipase C-gamma or induces intracellular calcium release.

In a further or alternative embodiment of such methods, the composition is administered in combination with an additional anticancer agent. In a further or alternative embodiment of such methods, the additional anticancer agent is a topical agent, antipruritic agent, mustard application, bone marrow transplant, stem cell transplant, surgery, phototherapy, chemotherapy, photochemotherapy, radiation therapy, immunotherapy, radioimmunotherapy, systemic therapy, or any combination thereof.

In a further or alternative embodiment of such methods, (a) the number of proliferative T-cells in the subject decreases by at least 50%, and/or (b) the size, number and shape of tumors or plaques or patches on the skin of the subject decreases by at least 50% after administering the therapeutically effective amount of the selective inhibitor of histone deacetylase 8 activity.

In a further or alternative embodiment of such methods, the subject is refractory or intolerant to at least one other treatment for a T-cell proliferative disorder.

A further or alternative embodiment of such methods also comprises administering to the subject a therapeutic agent to reduce side effects associated with the use of the composition.

In a further or alternative embodiment of such methods, the daily dosage of the composition to the subject is about 0.02 to about 5000 mg.

In another aspect are methods for treating a T-cell proliferative disorder, comprising administering to a subject in need a plurality of T-cells, wherein the T-cells are exposed ex vivo to a composition containing a selective inhibitor of histone deacetylase 8 activity at a concentration that is effective for selectively killing transformed T-cells.

In a further or alternative embodiment of such methods, the plurality of autologous T-cells is administered in combination with a composition containing a selective inhibitor of histone deacetylase 8 activity.

In a further or alternative embodiment of such methods, the selective inhibitor is a compound of formula Ia or IIa:

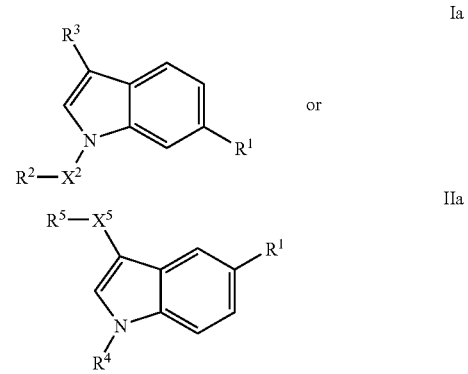

where
$R^1$ in Formula Ia or IIa is —C(O)NHOH;
$X^2$ is a bond, alkylene, or alkenylene where the alkylene or alkenylene is optionally substituted with one, two, three, four, or five halo;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;

$R^3$ is hydrogen, alkyl, substituted alkyl, alkenyl, substituted alkenyl, hydroxy, alkoxy, or haloalkoxy;

$R^4$ is hydrogen, alkyl, substituted alkyl, alkenyl, substituted alkenyl, hydroxy, alkoxy, haloalkoxy, or optionally substituted phenyl;

$X^5$ is a bond, alkylene, or alkenylene where the alkylene or alkenylene is optionally substituted with halo; and $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the selective inhibitor is a compound of Formula Ib or IIb:

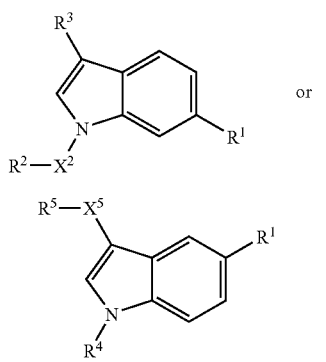

where $R^1$ in Formula Ib or IIb is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR— (where $R^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);

$R^4$ is hydrogen, alkyl, substituted alkyl, alkenyl, substituted alkenyl, hydroxy, alkoxy, haloalkoxy, or optionally substituted phenyl; and $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^1$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the plurality of autologous T-cells is administered in combination with at least one additional anticancer agent. In a further or alternative embodiment of such methods, the anticancer agent is a topical agent, antipruritic agent, mustard application, bone marrow transplant, stem cell transplant, surgery, phototherapy, chemotherapy, photochemotherapy, radiation therapy, immunotherapy, radioimmunotherapy, systemic therapy, or any combination thereof.

In another aspect are methods for predicting responsiveness to a treatment for a T-cell proliferative disorder, comprising: determining the level of histone deacetylase 8 activity in a biological sample from a subject having the T-cell proliferative disorder, and providing information that a higher level of the histone deacetylase 8 activity is indicative of the subject's higher likelihood of responsiveness to a composition containing a selective inhibitor of histone deacetylase 8 activity.

In a further or alternative embodiment of such methods, the selective inhibitor is a compound of formula Ia or IIa:

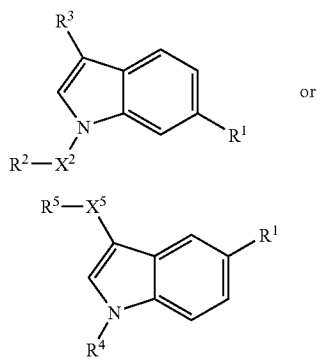

where
- $R^1$ in Formula Ia or IIa is —C(O)NHOH;
- $X^2$ is a bond, alkylene, or alkenylene where the alkylene or alkenylene is optionally substituted with one, two, three, four, or five halo;
- $R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
- $R^3$ is hydrogen, alkyl, substituted alkyl, alkenyl, substituted alkenyl, hydroxy, alkoxy, or haloalkoxy;
- $R^4$ is hydrogen, alkyl, substituted alkyl, alkenyl, substituted alkenyl, hydroxy, alkoxy, haloalkoxy, or optionally substituted phenyl;
- $X^5$ is a bond, alkylene, or alkenylene where the alkylene or alkenylene is optionally substituted with halo; and
- $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the selective inhibitor is a compound of Formula Ib or IIb:

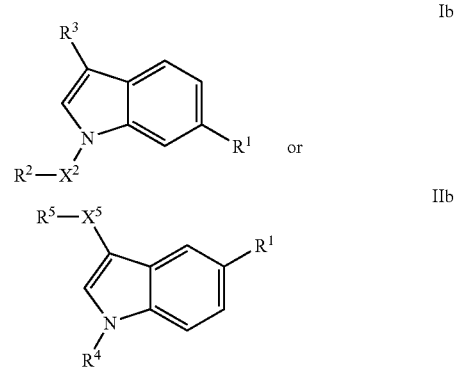

where
- $R^1$ in Formula Ib or IIb is —C(O)NHOH;
- $X^2$ is a bond, alkylene, or alkenylene where the alkylene or alkenylene is optionally substituted with one, two, three, four, or five halo;
- $R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;
- $R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S$(O)_{0-2}$—, alkenyl-S$(O)_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);
- $R^4$ is hydrogen, alkyl, substituted alkyl, alkenyl, substituted alkenyl, hydroxy, alkoxy, haloalkoxy, or optionally substituted phenyl; and
- $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the level of histone deacetylase 8 activity is determined by measuring the level of phospholipase C-gamma activity, mRNA, protein, or phospholipase C-gamma dependent changes in intracellular calcium levels. In a further or alternative embodiment of such methods, the composition further comprises an agent that activates phospholipase C-gamma or induces intracellular calcium release.

In another aspect are methods for predicting efficacy of a treatment for a T-cell proliferative disorder comprising: administering to a subject having a T-cell proliferative disorder a composition containing a selective inhibitor of histone deacetylase 8 activity; monitoring the subject's histone deacetylase 8 activity for an increase or decrease in activity; and utilizing the patient's histone deacetylase 8 activity as an indication for the amount of the next dosage of the compound.

In a further or alternative embodiment of such methods, the selective inhibitor is a compound of formula Ia or IIa:

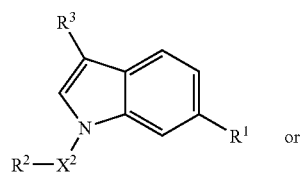

Ia

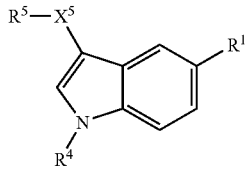

IIa where
$R^1$ in Formula Ia or IIa is —C(O)NHOH;
$X^2$ is a bond, alkylene, or alkenylene where the alkylene or alkenylene is optionally substituted with one, two, three, four, or five halo;
$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
$R^3$ is hydrogen, alkyl, substituted alkyl, alkenyl, substituted alkenyl, hydroxy, alkoxy, or haloalkoxy;
$R^4$ is hydrogen, alkyl, substituted alkyl, alkenyl, substituted alkenyl, hydroxy, alkoxy, haloalkoxy, or optionally substituted phenyl;
$X^5$ is a bond, alkylene, or alkenylene where the alkylene or alkenylene is optionally substituted with halo; and
$R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

A further or alternative embodiment of such methods further comprises adjusting the dosage of the composition administered to the subject.

In a further or alternative embodiment of such methods, the selective inhibitor is a compound of Formula Ib or IIb:

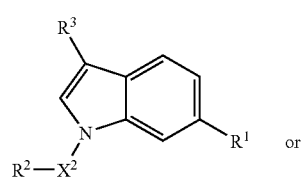

Ib

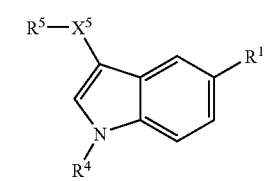

IIb where $R^1$ in Formula Ib or IIb is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR— (where $R^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where $R^a$ and $R^b$ are independently hydrogen, alkyl, substituted alkyl, alkenyl, alkynyl, substituted alkynyl, hydroxy, alkoxy, or alkenyloxy);

$R^4$ is hydrogen, alkyl, substituted alkyl, alkenyl, substituted alkenyl, hydroxy, alkoxy, haloalkoxy, or optionally substituted phenyl; and $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

In a further or alternative embodiment of such methods, the monitoring of the subject's histone deacetylase 8 activity comprises measuring the subject's phospholipase C activity, mRNA, protein level, or phospholipase C dependent changes in intracellular calcium levels.

In a further or alternative embodiment of such methods, the composition further contains an agent that activates phospholipase C or induces intracellular calcium release.

Unless otherwise stated, the following terms used in the specification and claims have the following meanings:

"Acyl" means a —C(O)R radical where R is alkyl, substituted alkyl, alkenyl, substituted alkenyl, alkoxy, haloalkyl, haloalkoxy, optionally substituted cycloalkyl, optionally substituted cycloalkylalkyl, optionally substituted aryl, optionally substituted aralkyl, optionally substituted heteroaryl, optionally substituted heteroaralkyl, optionally substituted heterocycloalkyl, or optionally substituted heterocycloalkylalkyl, as defined herein, e.g., acetyl, benzoyl, trifluoromethylcarbonyl, or 2-methoxyethylcarbonyl, and the like.

"Acylamino" means a —NRR' radical where R is hydrogen, hydroxy, alkyl, or alkoxy and R' is acyl, as defined herein.

"Acyloxy" means an —OR radical where R is acyl, as defined herein, e.g. cyanomethylcarbonyloxy, and the like.

"Administration" and variants thereof (e.g., "administering" a compound) in reference to a compound described herein means introducing the compound or a prodrug of the compound into the system of the animal in need of treatment for example, orally, bucally, transdermally, intranasally, intravenously, or rectally. When a compound described herein or prodrug thereof is provided in combination with one or more other active agents (e.g., estrogen receptor modulators, androgen receptor modulators, retinoid receptor modulators, cytotoxic agents, antiproliferative agents, etc.), "administration" and its variants are each understood to include concurrent and sequential introduction of the compound or prodrug thereof and other agents.

"Alkenyl" means a linear monovalent hydrocarbon radical of two to six carbon atoms or a branched monovalent hydrocarbon radical of three to six carbon atoms containing one or two double bonds e.g., ethenyl, propenyl (including all isomeric forms), 1-methylpropenyl, butenyl (including all isomeric forms), or pentenyl (including all isomeric forms), and the like.

"Alkenylcarbonyl" means a —C(O)R radical where R is alkenyl as defined herein.

"Alkenylcarbonyloxy" means a —OC(O)R radical where R is alkenyl as defined herein.

"Alkenylene" means a linear divalent hydrocarbon radical of two to six carbon atoms or a branched divalent hydrocarbon radical of three to six carbon atoms containing at least one, preferably one or two, double bonds e.g., ethen-1,2-diyl, propen-3,3-diyl, propen-1,3-diyl, or 2-methyl-but-2-en-1,4-diyl, and the like.

"Alkenyloxy" means an —OR radical where R is alkenyl as defined herein.

"Alkoxy" means a —OR radical where R is alkyl as defined herein, e.g., methoxy, ethoxy, propoxy, or 2-propoxy, n-, iso-, or tert-butoxy, and the like.

"Alkoxyalkyl" means an alkyl radical substituted with one, two, or three alkoxy group(s) as defined herein.

"Alkoxyalkyloxy" means a OR radical where R is alkoxyalkyl as defined herein.

"Alkoxycarbonyl" means a —C(O)OR radical where R is alkyl as defined herein, e.g., methoxycarbonyl, ethoxycarbonyl, and the like.

"Alkoxycarbonylamino" means a —NR'R" radical where R' is hydrogen, alkyl, alkenyl, hydroxy, or alkoxy as defined herein and R" is alkoxycarbonyl as defined herein.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like.

"Alkylamino" means a —NHR radical where R is alkyl as defined herein, e.g., methylamino, ethylamino, n-, iso-propylamino, n-, iso-, tert-butylamino, and the like.

"Alkylaminoalkyl" means an alkyl radical substituted with one or two alkylamino group(s) as defined herein.

"Alkylaminoalkyloxy" means an OR radical where R is alkylaminoalkyl as defined herein.

"Alkylaminocarbonyl" means a —C(O)R radical where R is alkylamino as defined herein e.g, methylaminocarbonyl or ethylaminocarbonyl, and the like.

"Alkylaminocarbonylamino" means a —NR'R" radical where R' is hydrogen, alkyl, alkenyl, hydroxy, or alkoxy and R" is alkylaminocarbonyl as defined herein.

"Alkylaminocarbonyloxy" means an —OR radical where R is alkylaminocarbonyl as defined herein.

"Alkylaminosulfonyl" means a —S(O)$_2$NHR radical where R is alkyl, as defined herein.

"Alkylcarbonyl" means a —C(O)R radical where R is alkyl as defined herein.

"Alkylcarbonylamino" means a —NR'C(O)R" radical where R' is hydrogen, alkyl, alkenyl, hydroxy, or alkoxy and R" is alkyl.

"Alkylcarbonyloxy" means a —OC(O)R radical where R is alkyl as defined herein.

"Alkylene" means a linear saturated divalent hydrocarbon radical of one to six carbon atoms or as otherwise indicated or a branched saturated divalent hydrocarbon radical of two to six carbon atoms or as otherwise indicated, e.g., methylene, prop-2,2-diyl, eth-1,2-diyl, prop-1,3-diyl, 1-methylprop-1,3-diyl, 2-methylprop-1,3-diyl, but-1,4-diyl (including all isomers), or pent-1,5-diyl (including all isomers), and the like. Alkylene may contain the number of carbon atoms indicated. For example the term (alkylene)$_{1-3}$ means alkylene containing from 1 carbon atom, i.e., methylene, to 3 carbon atoms, i.e., eth-1,2-diyl, eth-1,1-diyl, prop-1,3-diyl, 1-methyleth-1,2-diyl-, 2-methyleth-1,2-diyl, prop-1,1-diyl, and prop-2,2-diyl. The term (alkylene)$_0$ means that a bond is intended.

"Alkylsulfinyl" means an —S(O)R radical where R is alkyl as defined herein.

"Alkylsulfonyl" means a —SO$_2$R radical where R is alkyl as defined herein, e.g., methylsulfonyl or ethylsulfonyl, and the like.

"Alkylsulfonylamino" means a —NR'R" radical where R is hydrogen, alkyl, alkenyl, hydroxy, or alkoxy and R" is alkylsulfonyl as defined herein.

"Alkylthio" means an —SR radical where R is alkyl as defined herein.

"Alkynyl" means a linear monovalent hydrocarbon radical of two to six carbon atoms or a branched monovalent hydrocarbon radical of three to six carbon atoms containing at least one, preferably one or two, triple bond(s), e.g., ethynyl, propynyl (and all isomeric forms) and butynyl (and all isomeric forms), and the like.

"Amino" means a —NH$_2$, or an N-oxide derivative.

"Aminoalkyl" means an alkyl radical that is substituted with one or two amino group(s).

"Aminoalkoxy" means a —OR radical where R is aminoalkyl, as defined herein.

"Aminocarbonyl" means a —CONH$_2$ radical, or an N-oxide derivative, or a protected derivative thereof.

"Aminosulfonyl" means an —S(O)$_2$NH$_2$ radical.

"Aralkyl" means an alkyl radical substituted with an aryl group as defined herein.

"Aromatic" refers to a moiety wherein the constituent atoms make up an unsaturated ring system, all atoms in the ring system are sp$^2$ hybridized and the total number of pi electrons is equal to 4n+2.

"Aryl" means a monovalent, monocyclic or fused bicyclic hydrocarbon radical of 6 to 12 ring atoms, wherein the ring comprising a monocyclic radical ring is aromatic and wherein at least one of the fused rings comprising a bicyclic radical is aromatic. Fused bicyclic hydrocarbon radical includes bridged ring systems. Unless otherwise stated, the valency of the group may be located on any atom of any ring within the radical, valency rules permitting. More specifically the term aryl includes, but is not limited to, phenyl, naphthyl, indanyl (including, for example, indan-5-yl, or indan-2-yl, and the like) or tetrahydronaphthyl (including, for example, tetrahydronapth-1-yl, or tetrahydronapth-2-yl, and the like), and the like.

"Carboxy" means a —C(O)OH radical.

"Composition," as used herein, is intended to encompass a product comprising the specified ingredients in the specified amounts, as well as any product which results, directly or indirectly, from combination of the specified ingredients in the specified amounts.

"Cyanoalkyl" means an alkyl radical substituted with one or two cyano group(s).

"Cyanoalkylaminocarbonyl" means a —C(O)NR'R" radical where R' is hydrogen, alkyl, alkenyl, hydroxy, or alkoxy and R" is cyanoalkyl as defined herein.

"Cycloalkyl" means a monocyclic or fused bicyclic, saturated or partially unsaturated, monovalent hydrocarbon radical of three to ten carbon ring atoms. Fused bicyclic hydrocarbon radical includes bridged ring systems. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Dialkylamino" means a radical —NRR' where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl radical substituted with one or two dialkylamino group(s) as defined herein.

"Dialkylaminoalkyloxy" means an —OR radical where R is dialkylaminoalkyl as defined herein.

"Dialkylaminocarbonyl" means a —C(O)R radical where R is dialkylamino as defined herein, e.g, dimethylaminocarbonyl or methylethylaminocarbonyl, and the like.

"Dialkylaminocarbonylamino" means a —NR'R" radical where R' is hydrogen, alkyl, alkenyl, hydroxy, or alkoxy and R" is dialkylaminocarbonyl as defined herein.

"Dialkylaminocarbonyloxy" means an —OR radical where R is dialkylaminocarbonyl as defined herein.

"Dialkylaminosulfonyl" means an —S(O)$_2$NR'R" radical where R' and R" are alkyl.

"Halo" means fluoro, chloro, bromo, and iodo, preferably fluoro or chloro.

"Haloalkoxy" means a —OR radical where R is haloalkyl as defined herein e.g., —OCF$_3$, —OCHF$_2$, and the like.

"Haloalkyl" means alkyl as defined herein which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_3$, and the like.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, —N(R$^{200}$)—, —Si(alkyl)$_2$—, —P(=S)(R$^{201}$)—, and —P(=O)(R$^{201}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{200}$ is hydrogen, alkyl, hydroxy, alkoxy, acyl, or alkylsulfonyl. R$^{201}$ is alkyl, optionally substituted phenyl, optionally substituted phenylalkyl, optionally substituted cycloalkyl, or optionally substituted cycloalkylalkyl. Fused bicyclic radical includes bridged ring systems. Unless stated otherwise, the valency may be located on any atom of any ring of the heteroaryl group, valency rules permitting. In particular, when the point of valency is located on a nitrogen or phosphorous atom, R$^{200}$ or R$^{201}$, respectively, is absent. More specifically the term heteroaryl includes, but is not limited to, 1,2,4-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isooxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one or more, preferably one, two, three, or four ring heteroatoms independently selected from —O—, —S(O)$_n$— (n is 0, 1, or 2), —N—, —N(R$^{200}$)—, —Si(alkyl)$_2$—, —P(=S)(R$^{201}$)—, and —P(=O)(R$^{201}$)—, the remaining ring atoms being carbon. One or two ring carbon atoms may be replaced by a —C(O)—, —C(S)—, or —C(=NH)— group. R$^{200}$ is hydrogen, alkyl, hydroxy, alkoxy, acyl, or alkylsulfonyl. R$^{201}$ is alkyl, optionally substituted phenyl, optionally substituted phenylalkyl, optionally substituted cycloalkyl, or optionally substituted cycloalkylalkyl. Fused bicyclic radical includes bridged ring systems. Unless otherwise stated, the valency of the group may be located on any atom of any ring within the radical, valency rules permitting. In particular, when the point of valency is located on a nitrogen or phosphorous atom, R$^{200}$ or R$^{201}$, respectively, is absent. More specifically the term heterocycloalkyl includes, but is not limited to, pyrrolidinyl, 2,5-dihydro-1H-pyrrolyl, piperidinyl, morpholinyl, piperazinyl, tetrahydropyranyl, 2-oxopiperidinyl, and thiomorpholinyl, and the derivatives thereof and N-oxide or a protected derivative thereof.

"Hydroxyalkyl" means an alkyl radical substituted with one, two, or three hydroxy group(s).

"Hydroxyalkoxy" means an —OR radical where R is hydroxylalkyl as defined herein.

"IC$_{50}$," as used herein refers to an amount, concentration or dosage of a particular test compound that achieves a 50% inhibition of a maximal response, such as inhibition of HDAC8, in an assay that measures such response.

"Optionally substituted" or "may be substituted," when modifying a particular group, means that the group the term modifies may, but does not have to, be substituted. Where the term "optionally substituted" or "may be substituted" is used to modify a particular group, this does not mean, unless otherwise stated, that any other groups not so modified cannot also be optionally substituted. Furthermore, where a group is defined as being substituted by one of a number of enumerated alternative substitutents, it does not mean, unless otherwise stated, that the group cannot be substituted further with one or more substituents not enumerated. For example, "optionally substituted heterocycloalkyl" means that the heterocycloalkyl may but need not be substituted with the enumerated substituents within the definition of "optionally substituted heterocycloalkyl"; and the description includes situations where the heterocycloalkyl group is substituted and situations where the heterocycloalkyl group is not substituted.

"Optionally substituted aryl" means an aryl radical optionally substituted with one, two, or three group(s) selected from acyl, acylamino, acyloxy, alkyl, substituted alkyl, alkenyl, substituted alkenyl, alkynyl, substituted alkynyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, optionally substituted phenylsulfonylamino, aminoalkoxy, —P(O)ORR' (where R and R' are independently alkyl, optionally substituted cycloalkyl, optionally substituted phenyl, or optionally substituted heteroaryl), —P(O)RR' (where R and R' are independently alkyl, optionally substituted cycloalkyl, optionally substituted phenyl, or optionally substituted heteroaryl; or R and R' together with the P to which they are attached form optionally substituted heterocycloalkyl or optionally substituted heteroaryl), optionally substituted phenyl, and optionally substituted heteroaryl; or aryl is pentafluorophenyl. Within the optional substituents on "optionally substituted aryl", alkyl, alkenyl, and alkynyl, either alone or as part of another group (including, for example, the alkyl in heteroaralkyl), are independently optionally substituted with one, two, three, four, or five halo.

"Optionally substituted arylaminocarbonyl" means a —C(O)NR'R" radical where R' is hydrogen, alkyl, alkenyl, hydroxy, or alkoxy and R" is optionally substituted aryl, as defined herein.

"Optionally substituted arylcarbonylamino" means a —NR'C(O)R" radical where R' is hydrogen, alkyl, alkenyl, hydroxy, or alkoxy and R" is optionally substituted aryl as defined herein.

"Optionally substituted cycloalkyl" means a cycloalkyl radical optionally substituted with one, two, or three group(s) selected from acyl, acyloxy, acylamino, alkyl, substituted alkyl, alkenyl, substituted alkenyl, alkynyl, substituted alkynyl, alkoxy, alkoxycarbonyl, alkylthio, alkylsulfinyl, alkylsulfonyl, aminosulfonyl, alkylaminosulfonyl, dialkylaminosulfonyl, alkylsulfonylamino, optionally substituted phenylsulfonylamino, halo, hydroxy, amino, aminocarbonyl, alkylamino, dialkylamino, alkylaminocarbonyl, dialkylaminocarbonyl, nitro, alkoxyalkyloxy, aminoalkoxy, carboxy, cyano, optionally substituted phenyl, —P(O)ORR' (where R and R' are independently alkyl, cycloalkyl, optionally substituted aryl, or optionally substituted heteroaryl), —P(O)RR' (where R and R' are independently alkyl, cycloalkyl, optionally substituted aryl, or optionally substituted heteroaryl; or R and R' together with the P to which they are attached form optionally substituted heterocycloalkyl or optionally substituted heteroaryl), and optionally substituted heteroaryl. Within the above optional substitutents, the alkyl, alkenyl, and alkynyl, either alone or as part of another substituent on the optionally substituted cycloalkyl ring, are independently optionally substituted with one, two, three, four, or five halo, e.g. haloalkyl, haloalkoxy, haloalkenyloxy, or haloalkylsulfonyl.

"Optionally substituted cycloalkylalkyl" means an alkyl radical substituted with one or two optionally substituted cycloalkyl groups(s) as defined herein.

"Optionally substituted cycloalkylcarbonyl" means a —C(O)R radical where R is optionally substituted cycloalkyl as defined herein.

"Optionally substituted heteroaryl" means a heteroaryl radical optionally substituted with one, two, or three group(s) selected from alkyl, substituted alkyl, alkenyl substituted alkenyl, alkynyl, substituted alkynyl, acyl, acylamino, acyloxy, alkoxy, alkenyloxy, alkoxycarbonyl, alkylthio, halo, hydroxy, amino, alkylamino, dialkylamino, nitro, aminocarbonyl, alkylaminocarbonyl, dialkylaminocarbonyl, carboxy, cyano, alkylsulfinyl, alkylsulfonyl, optionally substituted phenylsulfonyl, aminosulfonyl, alkylaminosulfonyl, dialkylaminosulfonyl, alkylsulfonylamino, optionally substituted phenylsulfonylamino, aminoalkoxy, optionally substituted phenyl, optionally substituted heterocycloalkyl, —P(O)ORR' (where R and R' are independently alkyl, optionally substituted cycloalkyl, optionally substituted aryl, or heteroaryl), and —P(O)RR' (where R and R' are independently alkyl, optionally substituted cycloalkyl, optionally substituted aryl, or heteroaryl; or R and R' together with the P to which they are attached form optionally substituted heterocycloalkyl or heteroaryl). Within $R^{99}$, $R^{100}$, and the above optional substitutents, the alkyl, alkenyl, and alkynyl, either alone or as part of another substituent on the optionally substituted heteroaryl ring, are independently optionally substituted with one, two, three, four, or five halo, e.g. haloalkyl, haloalkoxy, or haloalkylsulfonyl.

"Optionally substituted heteroarylaminocarbonyl" means a —C(O)NR'R" radical where R' is hydrogen, alkyl, alkenyl, hydroxy, or alkoxy and R" is optionally substituted heteroaryl, as defined herein.

"Optionally substituted phenyl" means a phenyl radical optionally substituted with one, two, or three group(s) selected from acyl, acylamino, acyloxy, alkyl, substituted alkyl, alkenyl, substituted alkenyl, alkynyl, substituted alkynyl, alkoxy, alkenyloxy, halo, hydroxy, alkoxycarbonyl, alkenyloxycarbonyl, amino, alkylamino, dialkylamino, nitro, aminocarbonyl, alkylaminocarbonyl, dialkylaminocarbonyl, carboxy, cyano, alkylthio, alkylsulfinyl, alkylsulfonyl, aminosulfonyl, alkylaminosulfonyl, dialkylaminosulfonyl, alkylsulfonylamino, phenylsulfonylamino, aminoalkoxy, —P(O)ORR' (where R and R' are independently alkyl, optionally substituted cycloalkyl, optionally substituted aryl, or optionally substituted heteroaryl), —P(O)RR' (where R and R' are independently alkyl, optionally substituted cycloalkyl, optionally substituted aryl, or optionally substituted heteroaryl; or R and R' together with the P to which they are attached form optionally substituted heterocycloalkyl or optionally substituted heteroaryl), optionally substituted aryl, and optionally substituted heteroaryl; or optionally substituted phenyl is pentafluorophenyl. Within the optional substituents on "optionally substituted phenyl", alkyl, alkenyl, and alkynyl, either alone or as part of another group (including, for example, the alkyl in heteroaralkyl), are independently optionally substituted with one, two, three, four, or five halo.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

A "selective HDAC8 inhibitor," as used herein, refers to a compound that has an $IC_{50}$ for inhibition of HDAC8 acetyltransferase activity that is at least 5 fold to more than 500 fold lower than for the acetyltransferase activity of another HDAC. In some embodiments, the selective HDAC8 inhibitor has an $IC_{50}$ for HDAC8 acetyltransferase activity that is about 5, 10, 50, 100, 150, 200, 250, 300, 350, 400, 450 or more than 500 fold lower than the $IC_{50}$ for acetyltransferase activity of another HDAC. In one embodiment, the selective HDAC8 inhibitor has an $IC_{50}$ for HDAC8 activity that is at least 10 fold lower than the $IC_{50}$ for HDAC1, HDAC2, HDAC3, HDAC6, HDAC10, and HDAC11.

A "subject," as referred to herein, can be any vertebrate (e.g., a mouse, rat, cat, guinea pig, hamster, rabbit, zebrafish, dog, non-human primate, or human) unless specified otherwise.

"Substituted alkenyl" means an alkenyl radical, as defined herein, substituted with one or more group(s), preferably one, two, or three groups, independently selected from alkylcarbonyl, alkenylcarbonyl, optionally substituted cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-S(O)0-2—, alkenyl-S(O)0-2—, aminosulfonyl, alkylaminosulfonyl, dialkylaminosulfonyl, alkylsulfonyl-NRc- (where Rc is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NRaRb (where Ra and Rb are independently hydrogen, alkyl, substituted alkyl, alkenyl, alkynyl, substituted alkynyl, hydroxy, alkoxy, or alkenyloxy).

"Substituted alkyl" means an alkyl radical, as defined herein, substituted with one or more group(s), preferably one, two, or three groups, independently selected from alkylcarbonyl, alkenylcarbonyl, optionally substituted cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, alkenyl, substituted alkenyl, alkynyl, substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, alkenyl, substituted alkenyl, alkynyl, substituted alkynyl, hydroxy, alkoxy, alkenyloxy, or cyanoalkyl).

"Substituted alkynyl" means an alkynyl radical, as defined herein, substituted with one or more group(s), preferably one, two, or three groups, independently selected from alkylcarbonyl, alkenylcarbonyl, optionally substituted cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, halo, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkenyl, alkynyl, substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, substituted alkyl, alkenyl, substituted alkenyl, alkynyl, hydroxy, alkoxy, alkenyloxy, or cyanoalkyl).

A "therapeutically effective amount," as used herein, refers to the amount of an agent or compound that confers a desired effect on an individual subject, a subset of patients, or a general population of patients with one or more T-cell proliferative disorders. A desired effect can include, for example, reducing and/or alleviating at least one sign, symptom, or cause associated with the disease, stabilizing a condition, improving the quality of life, or any other desired alteration of a biological system. An appropriate therapeutically effective amount can be determined, by way of example, in a phase III clinical study to provide a therapeutic benefit to patients having T-cell proliferative disorders, and can be determined by, for example, statistical analyses, dose escalation studies, or the like. A therapeutically effective amount may include a prophylactically effective amount. It is understood that a therapeutically effective amount can vary from subject to subject, due to, for example, variation in metabolism, age, weight, general condition of the subject, the condition being treated, the severity of the condition being treated, or the judgment of the prescribing physician.

"Treating" or "treatment" of a disease includes:

(1) preventing the disease, i.e. causing any of the clinical symptoms of the disease not to develop in a subject that may be exposed to or predisposed to the disease but does not yet experience or display symptoms of the disease;

(2) inhibiting the disease, i.e., arresting or reducing the development of the disease or any of its clinical symptoms; or (3) relieving the disease, i.e., causing regression of the disease or any of its clinical symptoms.

The selective HDAC8 inhibitors used in the methods described herein include N-oxide derivatives and protected derivatives of compounds of Formula (Ia), (IIa), (Ib), and (IIb). For example, when compounds of Formula (Ia), (IIa), (Ib), and (IIb) contain an oxidizable nitrogen atom, the nitrogen atom can be converted to an N-oxide by methods well known in the art. Also, when compounds of Formula (Ia), (IIa), (Ib), and (IIb) contain groups such as hydroxy, carboxy, thiol or any group containing a nitrogen atom(s), these groups can be protected with a suitable protecting group. A comprehensive list of suitable protective groups can be found in T. W. Greene, *Protective Groups in Organic Synthesis*, John Wiley & Sons, Inc. 1999, the disclosure of which is incorporated herein by reference in its entirety. The protected derivatives of compounds of Formula (Ia), (IIa), (Ib), and (IIb) can be prepared by methods well known in the art.

The compounds used in the methods described herein may have asymmetric centers. Such compounds containing an asymmetrically substituted atom may be isolated in optically active or racemic forms. It is well known in the art how to prepare optically active forms, such as by resolution of materials. All chiral, diastereomeric, racemic forms are contemplated for use in the methods described herein, unless the specific stereochemistry or isomeric form is specifically indicated.

Certain compounds of Formula (Ia), (IIa), (Ib), and (IIb) can exist as isomers. All possible isomers are contemplated for use in the methods described herein. Additionally, as used herein, the terms alkyl, alkylene, alkenylene, and alkynylene include all the possible isomeric forms albeit only a few examples are set forth. Furthermore, when the cyclic groups such as aryl, heteroaryl, heterocycloalkyl are substituted, they include all the positional isomers albeit only a few examples are set forth.

Throughout the specification, groups and substituents thereof can be chosen by one skilled in the field to provide stable moieties and compounds.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Other features, objects, and advantages will be apparent from the description and from the claims. The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8 is an illustrative series of bar graphs that show (A) the effect of a calcium effector (thapsigargin; 0.2 µM) or (B) a calcium chelator (BAPTA-AM; 0.5 µM) on the induction of apoptosis by compound 23 (10 µM) in wild-type (Jurkat) versus J.γ1 (J.gamma1) Jurkat cells.

DETAILED DESCRIPTION OF THE INVENTION

Figure 1:
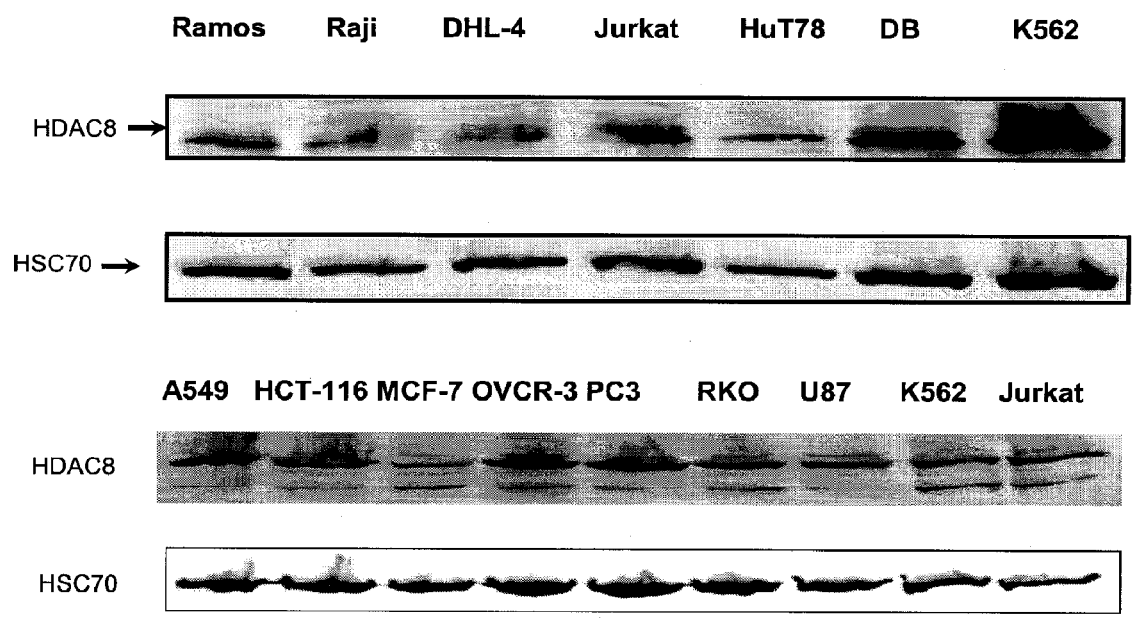
FIG. 1 is an illustrative immunoblot showing HDAC8 expression in a series of cell lines. For each cell line, Hsc 70 expression is also shown as a normalization control for apparent HDAC8 expression levels.

T-cell proliferative disorders arise where the T-cells grow abnormally. The T-cell proliferative disease can be, e.g., peripheral T cell lymphoma, lymphoblastic lymphoma, cutaneous T cell lymphoma, NK/T-cell lymphoma, adult T cell leukemia/lymphoma, T-cell acute lymphoblastic leukemia (T-ALL), T-cell chronic lymphoblastic leukemia (T-CLL), anaplastic large cell lymphoma, angioimmunoblastic T-cell lymphoma, enteropathy-type T-cell lymphoma, hepatosplenic T-cell lymphoma, mycosis fungoides/Sezary syndrome, or subcutaneous panniculitis-like T-cell lymphoma. Current treatments for T-cell proliferative diseases include topical treatments, antipruritic treatments, bone marrow or stem cell transplants, surgery, phototherapy, chemotherapy, photochemotherapy, radiation therapy, immunotherapy, radioimmunotherapy, systemic therapy, or any combination thereof.

Methods for determining HDAC activity in vivo or in vitro are known in the art, as disclosed in, e.g., Kim et al. (2006), *Methods Mol. Biol.*, 325:273-283. HDAC8 is expressed at high levels in tumor cell lines, e.g., Jurkat, HuT78, K562, PC3, and OVCAR-3. In fact, as described herein, inhibiting HDAC8 activity decreases proliferation of T-cell derived tumor cells (e.g., Jurkat cells) by apoptosis. Jurkat cells are human T-cell leukemia established from the peripheral blood of a 14 year old boy with acute lymphoblastic leukemia. In contrast, HDAC8 inhibition does not affect the proliferation of either non-cancerous cells (e.g., peripheral blood mononuclear cells) or tumor cell lines other than T-cell derived lines. Thus, selective HDAC8 inhibitors are useful for slowing or arresting the progression of T-cell derived cancers with lessened or no toxicity to non-cancerous cells.

One aspect described herein relates to a method for treating a T-cell proliferative disorder, including the step of administering to a subject in need a pharmaceutical composition containing a therapeutically effective amount of a selective HDAC8 inhibitor. The treatment can include, in addition to a selective HDAC8 inhibitor pharmaceutical composition, administering one or more additional anti-cancer agents described herein such as a topical agent, antipruritic agent, mustard application, bone marrow transplant, stem cell transplant, surgery, phototherapy, chemotherapy, photochemotherapy, radiation therapy, immunotherapy, radioimmunotherapy, or systemic therapy, in any combination.

Another aspect described herein relates to treating T-cell proliferative diseases by administering to a subject in need a plurality of autologous T-cells that have been exposed to a pharmaceutical composition containing a selective HDAC8 inhibitor ex vivo. T-cells from a donor subject suffering a T-cell proliferative disorder are cultured and expanded ex vivo in the presence of a selective HDAC8 inhibitor at a concentration that is effective for selectively killing transformed T-cells. Afterwards, the expanded T-cell population, free of transformed T-cells, can be introduced into the subject in need. T-cell culture, in vitro expansion, and in vivo transfer is described in, e.g., Porter et al. (2006), *Blood*, 107(4):1325-1331; Rapoport et al. (2005), *Nat. Med.,* 1230-1237; Laport et al. (2003), *Blood,* 102(6):2004-2013. The expanded T-cell population free of transformed T-cells can also be introduced into the subject in need in combination with a composition containing a selective HDAC8 inhibitor, or another anticancer agent in any combination.

Another aspect described herein relates to predicting a subject's responsiveness to a treatment for a T-cell proliferative disorder, by determining the level of HDAC8 activity in a biological sample from the subject, and providing information that the level of HDAC8 activity indicates the subject's responsiveness to a selective HDAC8 inhibitor pharmaceutical composition. Levels of HDAC8 activity can be indicated by various means, including, for example, by measuring mRNA or protein levels, phospholipase C-gamma activity, or intracellular calcium levels. Regardless of the method employed to measure levels of HDAC8 activity of a subject, one can correlate such levels of HDAC8 to a subject's responsiveness to a composition containing a selective HDAC8 inhibitor and obtain useful and concrete information on a patient's treatment efficacy. Information on a subject's responsiveness to a selective HDAC8 inhibitor pharmaceutical composition includes, for example, any interpretation of data regarding the subject's HDAC8 activity, information on how to interpret the subject's HDAC8 activity levels, references on HDAC8 activity, charts, data, graphical interpretations, or any other indication for determining a subject's HDAC8 activity level. By way of example, such information can be in the form of a test result, a write up, an oral discussion, presentation, or the like.

Another aspect described herein relates to a method for predicting efficacy of a treatment for a T-cell proliferative disorder. The method includes administering to a subject a composition containing a selective HDAC8 inhibitor, monitoring the subject's HDAC8 activity for an increase or decrease in activity, and utilizing the HDAC8 activity level as an indication for the amount of the next dosage of the composition. The methods herein are useful for indicating to a clinician a need to monitor a subject for efficacy of a treatment for a T-cell proliferative disorder, and to adjust a dosage of a composition containing a selective HDAC8 inhibitor as desired. For example, if it is determined that a subject suffering from a T-cell proliferative disorder has a high or increasing level of HDAC8 activity, one skilled in the art could determine that the dosage of a composition containing a selective HDAC8 inhibitor should be increased. If it is determined that a subject's HDAC8 activity level is low or decreasing, one skilled in the art can determine that the dosage of a composition containing a selective HDAC8 inhibitor should be maintained or decreased. Based on measuring the HDAC8 activity levels and assessing the responsiveness of a subject to a therapy including a composition containing a selective HDAC8 inhibitor, one skilled in the art can determine whether a dose of such composition should be maintained, increased, or decreased. The methods herein allow, for example, a clinician to provide an individually optimized dosage of a composition containing a therapeutically effective amount of selective HDAC8 inhibitor, so as to achieve a target level of HDAC8 activity in a particular patient having a T-cell proliferative disorder. By way of example, a clinician may utilize a subject's HDAC8 activity level as one factor indicating the amount of the subject's next dosage of the composition, but does not necessarily need to take the activity level into consideration.

Examples of Selective HDAC8 Inhibitors

In the following description of selective HDAC8 inhibitors suitable for use in the methods described herein, definitions of standard chemistry terms may be found in reference works (if not otherwise defined herein), including Carey and Sundberg, *Advanced Organic Chemistry,* 4th Ed., Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for HDAC8 are known in the art as disclosed in, e.g., U.S. Pat. No. 6,875,598. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The selective HDAC8 inhibitor for use in the methods described herein can be a compound of Formula Ia or IIa:

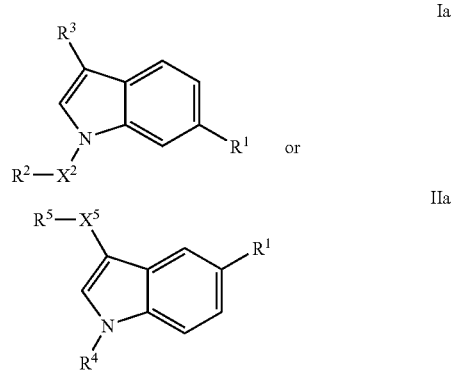

where $R^1$ in Formula Ia or IIa is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;

$R^3$ is hydrogen, alkyl, substituted alkyl, alkenyl, substituted alkenyl, hydroxy, alkoxy, or haloalkoxy;

$R^4$ is hydrogen, alkyl, substituted alkyl, alkenyl, substituted alkenyl, hydroxy, alkoxy, haloalkoxy, or optionally substituted phenyl;

$X^1$ is a bond, alkylene, or alkenylene where the alkylene or alkenylene is optionally substituted with halo; and $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

The selective inhibitor of HDAC8 can be a compound of Formula Ib or IIb:

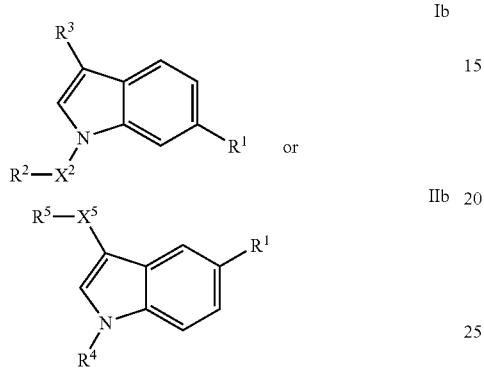

where $R^1$ in Formula Ib or IIb is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkenylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);

$R^4$ is hydrogen, alkyl, substituted alkyl, alkenyl, substituted alkenyl, hydroxy, alkoxy, haloalkoxy, or optionally substituted phenyl; and $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

Representative Compounds of Formula Ia and Ib

Selected compounds for use in the compositions and methods described herein are provided in Table 1, having Formula Ia and/or Ib:

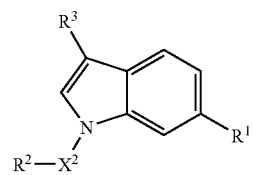

where $R^1$ is —C(O)NHOH, $R^3$ is hydrogen, and $X^2$ and $R^2$ are defined below.

TABLE 1

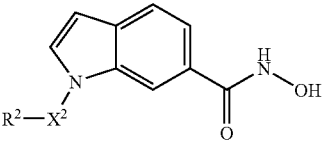

| Cmpd. No. | R² | X² |
|---|---|---|
| 1 | 3,4-dichlorophenyl | —CH$_2$— |
| 2 | 2-methylphenyl | —CH$_2$— |
| 3 | 3,4,5-trimethoxyphenyl | —CH$_2$— |
| 4 | 3-fluorophenyl | —CH$_2$— |
| 5 | 3-methylphenyl | —CH$_2$— |
| 6 | phenyl | —CH$_2$— |
| 7 | 3,5-dimethoxyphenyl | —CH$_2$— |
| 8 | phenyl | —CH(CH$_3$)— |
| 9 | 4-fluorophenyl | —CH$_2$— |
| 10 | 2-fluorophenyl | —CH$_2$— |
| 11 | 2-chlorophenyl | —CH$_2$— |
| 12 | 3-methoxyphenyl | —CH$_2$— |
| 13 | naphth-2-yl | —CH$_2$— |
| 14 | phenyl | —(CH$_2$)$_3$— |
| 15 | cyclohexyl | —CH$_2$— |
| 16* | phenyl | —CH=CHCH$_2$— |
| 17 | 4-(trifluoromethoxy)-phenyl | —CH$_2$— |
| 18 | 4-chlorophenyl | —CH$_2$— |
| 19 | benzo[2,1,3]oxadiazol-5-yl | —CH$_2$— |
| 20 | 4-methylphenyl | —CH$_2$— |
| 21 | 3-fluoro-4-methoxy-phenyl | —CH$_2$— |
| 22 | 4-(difluoromethoxy)-phenyl | —CH$_2$— |
| 23 | 4-methoxyphenyl | —CH$_2$— |
| 24 | phenyl | —CH$_2$CH$_2$— |
| 25 | 3-chlorophenyl | —CH$_2$— |
| 26 | N-(t-butoxycarbonyl)piperidin-4-yl | —CH$_2$— |
| 27 | piperidin-4-yl | —CH$_2$— |

*This compound is trans.

and are named 1-(3,4-dichloro-phenylmethyl)-1H-indole-6-carboxylic acid hydroxyamide; 1-(2-methyl-phenylmethyl)-1H-indole-6-carboxylic acid hydroxyamide; 1-(3,4,5-trimethoxy-phenylmethyl)-1H-indole-6-carboxylic acid hydroxyamide; 1-(3-fluoro-phenylmethyl)-1H-indole-6-carboxylic acid hydroxyamide; 1-(3-methyl-phenylmethyl)-1H-indole-6-carboxylic acid hydroxyamide; 1-(benzyl)-1H-indole-6-carboxylic acid hydroxyamide; 1-(3,5-dimethoxy-phenylmethyl)-1H-indole-6-carboxylic acid hydroxyamide; 1-(1-methyl-1-phenylmethyl)-1H-indole-6-carboxylic acid hydroxyamide; 1-(4-fluoro-phenylmethyl)-1H-indole-6-carboxylic acid hydroxyamide; 1-(2-fluoro-phenylmethyl)-1H-indole-6-carboxylic acid hydroxyamide; 1-(2-chloro-phenylmethyl)-1H-indole-6-carboxylic acid hydroxyamide; 1-(3-methoxy-phenylmethyl)-1H-indole-6-carboxylic acid hydroxyamide; 1-(naphth-2-ylmethyl)-1H-indole-6-carboxylic acid hydroxyamide; 1-(3-phenylpropyl)-1H-indole-6-carboxylic acid hydroxyamide; 1-(cyclohexylmethyl)-1H-indole-6-carboxylic acid hydroxyamide; 1-[1-(phenyl)-propen-3-yl]-1H-indole-6-carboxylic acid hydroxyamide; 1-[4-(trifluoromethoxy)-phenylmethyl]-1H-indole-6-carboxylic acid hydroxyamide; 1-(4-chloro-phenylmethyl)-1H-indole-6-carboxylic acid hydroxyamide; 1-(benzo[2,1,3]oxadiazol-5-ylmethyl)-1H-indole-6-carboxylic acid hydroxyamide; 1-(4-methyl-phenylmethyl)-1H-indole-6-carboxylic acid hydroxyamide; 1-(3-fluoro-4-methoxy-phenylmethyl)-1H-indole-6-carboxylic acid hydroxyamide; 1-[4-(difluoromethoxy)-phenylmethyl]-1H-indole-6-carboxylic acid hydroxyamide; 1-(4-methoxy-phenylmethyl)-1H-indole-6-carboxylic acid hydroxyamide; 1-(phenethyl)-1H-indole-6-carboxylic acid hydroxyamide; 1-(3-chloro-phenylmethyl)-1H-indole-6-carboxylic acid hydroxyamide; 1-[N-(t-butoxycarbonyl)piperidin-4-ylmethyl]-1H-indole-6-carboxylic acid hydroxyamide; and 1-(piperidin-4-ylmethyl)-1H-indole-6-carboxylic acid hydroxyamide.

Another select group of compounds for use in the compositions and methods described herein are provided in Table 2, having Formula Ia and/or IIb:

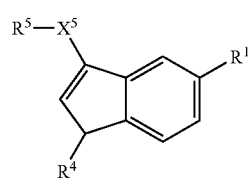

II where R$^1$ is —C(O)NHOH, X$^5$ is —CH$_2$—, and R$^4$ and R$^5$ are defined below.

TABLE 2

| Cmpd. No. | R⁴ | R⁵ |
|---|---|---|
| 28 | methyl | 4-nitrophenyl |
| 29 | ethyl | Phenyl |
| 30 | methyl | 4-(phenylcarbonylamino)-phenyl |
| 31 | isopropyl | phenyl |
| 32 | methyl | 4-aminophenyl |
| 33 | methyl | 4-fluorophenyl |
| 34 | phenyl | phenyl |
| 35 | methyl | 4-(t-butoxycarbonyl)piperazin-1-yl | and are named 1-methyl-3-(4-nitro-phenylmethyl)-1H-indole-5-carboxylic acid hydroxyamide; 1-ethyl-3-(phenylmethyl)-1H-indole-5-carboxylic acid hydroxyamide; 1-methyl-3-[4-(phenylcarbonylamino)-phenylmethyl]-1H-indole-5-carboxylic acid hydroxyamide; 1-isopropyl-3-(phenylmethyl)-1H-indole-5-carboxylic acid hydroxyamide; 1-methyl-3-(4-amino-phenylmethyl)-1H-indole-5-carboxylic acid hydroxyamide; 1-methyl-3-(4-fluoro-phenylmethyl)-1H-indole-5-carboxylic acid hydroxyamide; 1-phenyl-3-(phenylmethyl)-1H-indole-5-carboxylic acid hydroxyamide; and 1-methyl-3-[4-(t-butoxycarbonyl)piperazin-1-ylmethyl]-1H-indole-5-carboxylic acid hydroxyamide.

Examples of Pharmaceutical Compositions and Methods of Administration

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceu-* tical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

Provided herein are pharmaceutical compositions that include a compound described herein, such as, compounds of Formula (Ia), Formula (IIa), Formula (Ib), or Formula (IIb), and a pharmaceutically acceptable diluent(s), excipient(s), or carrier(s). In addition, the compounds described herein can be administered as pharmaceutical compositions in which compounds described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

A pharmaceutical composition, as used herein, refers to a mixture of a compound described herein, such as, for example, compounds of Formula (Ia), Formula (IIa), Formula (Ib), or Formula (IIb), with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a subject in need. Preferably, the subject is a human. A therapeutically effective amount can vary widely depending on the severity of the disease, the age and relative health of the subject, the potency of the compound used and other factors. The compositions can be used singly or in combination with one or more other agents as components of mixtures.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of Formula (Ia), Formula (IIa), Formula (Ib), or Formula (IIb), as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

Examples of Methods of Dosing and Treatment Regimens

The compositions containing the compound(s) described herein can be administered to a subject suffering from at least one symptom of a T-cell proliferative disorder, including for example, peripheral T cell lymphoma, lymphoblastic lymphoma, cutaneous T cell lymphoma, NK/T-cell lymphoma, adult T cell leukemia/lymphoma, T-cell acute lymphoblastic leukemia (T-ALL), T-cell chronic lymphoblastic leukemia (T-CLL), anaplastic large cell lymphoma, angioimmunoblastic T-cell lymphoma, enteropathy-type T-cell lymphoma, hepatosplenic T-cell lymphoma, mycosis fungoides/Sezary syndrome, or subcutaneous panniculitis-like T-cell lymphoma. Amounts effective for these uses may depend on the severity and course of the disease or condition, previous therapy, the subject's health status, weight, or response to the drugs, or the judgment of the treating physician. It is considered well within the skill of the art for one to determine such therapeutically effective amounts by routine experimentation (e.g., statistical analyses or dose escalation clinical trials).

Compositions containing the compounds described herein can also be administered to a patient susceptible to or otherwise at risk of a T-cell proliferative disorder. Amounts effective for this use may depend on the patient's state of health, weight, and the like. When used in a patient, amounts for this use will depend on the severity and course of the disease, disorder or condition, previous therapy, the subject's health status and response to the drugs, and the judgment of the treating physician. It is considered well within the skill of the art for one to determine such therapeutically effective amounts by routine experimentation (e.g., statistical analyses or dose escalation clinical trials).

Typical measures of improvement after being treated for a T-cell proliferative disorder include, for example, a decrease in the number of proliferative T-cells in the subject by 50% after the administration of at least one therapy, or by decreases in the size, number and shape of tumors or plaques or patches on the skin.

In the case wherein the subject's condition does not improve, upon the doctor's discretion the administration of the compounds may be administered chronically, that is, for an extended period of time, including throughout the duration of the subject's life in order to ameliorate or otherwise control or limit the symptoms of the subject's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the subject's conditions has occurred, a maintenance dose can be administered. Subsequently, the dosage or the frequency of administration, or both, can be reduced, as a function of the symptoms, to a level at which the improved condition is retained. Intermittent treatment on a long-term basis may also be pursued upon any recurrence of symptoms.

The amount of a given composition containing a therapeutically effective amount of a selective inhibitor of HDAC8 will vary depending upon factors such as the particular compound, the type of T-cell proliferative disorder or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, or the subject or host being treated. In general, however, doses employed for adult human treatment will typically be in the range of 0.02-5000 mg per day, preferably 1-1500 mg per day, or about 0.01 to 2.5 mg/kg body weight. The desired dose may conveniently be presented in a single dose or as divided doses administered simultaneously (or over a short period of time) or at appropriate intervals, for example as two, three, four or more sub-doses per day or in extended release form.

In unit (single) dosage form, the formulation is divided into unit doses containing appropriate quantities of one or more compound. Suitable unit dosage forms for oral administration include from about 1 to 50 mg active ingredient. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner. It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

Toxicity and therapeutic efficacy of the compositions described herein can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

Examples of Combination Treatments

The compositions containing a selective HDAC8 inhibitor described herein can also be used in combination with other agents. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

As disclosed herein, it may be appropriate to administer a composition containing a therapeutically effective amount of a selective HDAC8 inhibitor in combination with an agent that activates phospholipase C or induces intracellular calcium release. As further disclosed herein, it may also be appropriate to administer at least one composition described herein in combination with a therapeutic agent to reduce side effects associated with the use of the composition. By way of example only, if one of the side effects experienced by a patient upon receiving one of the compounds herein, such as a compound of Formula (Ia), Formula (IIa), Formula (Ib), or Formula (IIb) is nausea, then it may be appropriate to administer an anti-nausea agent in combination with the initial composition. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a subject may be increased by administering one of the compounds described herein with a therapeutic agent (which also includes a therapeutic regimen) that has therapeutic benefit. In any case, regardless of the disease, disorder or condition being treated, the overall benefit experienced by the patient may simply be additive of the two or the subject may experience a synergistic benefit.

As further disclosed herein, a composition containing a selective HDAC8 inhibitor can be used to treat a subject suffering from a T-cell proliferative disorder in any combination with one or more additional anti-cancer agents, such as a topical agent, antipruritic agent, mustard application, bone marrow transplant, stem cell transplant, surgery, phototherapy, chemotherapy, photochemotherapy, radiation therapy, immunotherapy, radioimmunotherapy, or systemic therapy.

Examples of such anticancer agents include, e.g., topical steroids, BCNU (Carmustine), nitrogen mustards, photo therapy, topical imiquimod, EBD, MTX, doxorubicin (Doxil), gemcitibine, etoposide, pentostatin, cytokines, interferon, 5-aza-2'-deoxycytidine, all trans retinoic acid, doxorubicin, vincristine, etoposide, gemcitabine, imatinib (Gleevec®), 17-N-Allylamino-17-Demethoxygeldanamycin (17-AAG), flavopiridol, LY294002, bortezomib, trastuzumab, BAY 11-7082, PKC412, or PD184352 in any combination.

Other examples of anticancer agents include Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Other examples of anti-cancer agents that can be employed in combination with a selective HDAC8 inhibitor include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacmme; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of anti-cancer agents that can be employed in combination with a selective HDAC8 inhibitor include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; inimunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; mynaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other examples of anticancer agents that can be employed in combination with a selective HDAC8 inhibitor include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful as anticancer agents in combination with a composition containing a selective HDAC8 inhibitor include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed as anticancer agents in combination with a composition containing a selective HDAC8 inhibitor include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful as anticancer agents in combination with a composition containing a selective HDAC8 inhibitor include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other examples of anticancer agents that can be used in in combination with a composition containing a selective HDAC8 inhibitor include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a composition containing a selective HDAC8 inhibitor include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

The particular choice of compositions and/or agents used will depend upon the diagnosis of the attending physicians and their judgment of the condition of the patient and the appropriate treatment protocol. The compositions and/or agents may be administered concurrently (e.g., simultaneously, essentially simultaneously or within the same treatment protocol) or sequentially, depending upon the nature of the disease, disorder, or condition, the condition of the patient, and the actual choice of compositions and/or agents used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically effective dosages can vary when the compositions are used in treatment combinations. Methods for experimentally determining therapeutically effective dosages of compositions and/or agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compositions and/or agents will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple compositions and/or agents (one of which is a compound of Formula Ia, Ib, IIa, or IIb described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations is also envisioned.

The agents which make up the combination therapy disclosed herein may be a combined dosage form or in separate dosage forms intended for substantially simultaneous administration. The agents that make up the combination therapy may also be administered sequentially, with either therapeutic agent being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

The compositions of containing a selective HDAC inhibitor described herein and combination therapies can be administered before, during or after the occurrence of a disease or condition, and the timing of administering the composition containing a compound can vary. Thus, for example, the compositions can be used as a prophylactic and can be administered continuously to subjects with a propensity to develop conditions or diseases in order to prevent the occurrence of the disease or condition. The compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A composition is preferably administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the composition containing the compound can be administered for at least 2 weeks, preferably about 1 month to about 5 years, and more preferably from about 1 month to about 3 years.

EXAMPLES

The following specific examples are to be construed as merely illustrative, and not limitative of the remainder of the disclosure in any way whatsoever.

Example 1

HDAC8 is Expressed in Tumor Cell Lines, and its Knock-Down Results in Apoptosis

HDAC8 expression was determined by immunoblotting and quantitative RT-PCR (Q-PCR) in a variety of tumor cell lines including the Ramos, Raji, DHL4, Jurkat, HuT78, DB, K562, A549, HCT-116, MCF-7, OVCR-3, PC3, RKO, and U87 cell lines.

HDAC8 expression was detected by in all tumor cell lines (FIG. 1), in contrast to the highly restricted expression pattern observed in normal tissues.

Figure 2:
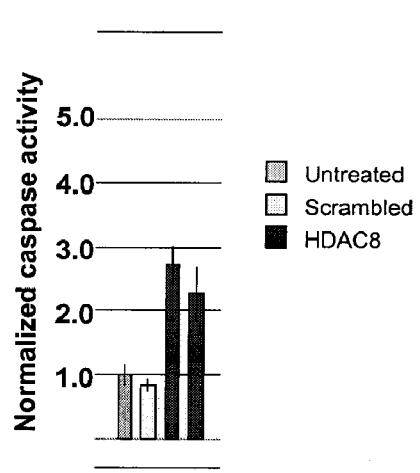
FIG. 2 is an illustrative bar graph showing the effect of RNAi knock-down of HDAC8 on apoptosis in HeLa cells.

RNAi knockdown of HDAC8 in HeLa cells was shown to induce apoptosis as demonstrated by increased caspase activity (FIG. 2)

Example 2

Selective HDAC8 Inhibitor Compounds

Candidate selective HDAC8 inhibitor compounds, Compound 23 and Compound 33 were assayed for their ability to inhibit, in vitro, HDAC8, as well as HDACs 1, 2, 3, 6, and 10. For comparison, broad spectrum HDAC inhibitors, CRA-024781 and SAHA, were also assayed in parallel. The results are summarized in Table 3 below. Compound 23 and Compound 33 have HDAC8 $IC_{50}$ values that are approximately 300 and 15 fold lower, respectively, than the next lowest HDAC target $IC_{50}$. (as a reference for $IC_{50}$ determination see Schultz et. al., Biochemistry 43, 11083-11091).

TABLE 3

Comparison of HDAC $IC_{50}$ values for pan-HDAC vs HDAC8-selective inhibitors

| | HDAC-1 (µM) | HDAC-2 (µM) | HDAC-3 (µM) | HDAC-6 (µM) | HDAC-8 (µM) | HDAC-10 (µM) |
|---|---|---|---|---|---|---|
| CRA-024781 (broad spectrum) | 0.005 | 0.019 | 0.008 | 0.017 | 0.19 | 0.024 |
| SAHA (broad spectrum) | 0.028 | 0.06 | 0.044 | 0.022 | 0.41 | 0.04 |
| Compound 33 | 2.6 | 23 | 1.5 | 0.36 | 0.024 | 5.3 |
| Compound 23 | 4 | >50 | >50 | 2.9 | 0.010 | 13 |

Based on these data, it was concluded that Compound 23 and Compound 33 are selective inhibitors of HDAC8.

Example 3

Compound 23 is Selectively Cytotoxic to T-Cell Derived Tumor Cell Lines

The ability of HDAC8-selective inhibitor compound, Compound 23, to reduce tumor cell proliferation in vitro was determined for several cell lines and peripheral blood mononuclear cells (PBMCs).

Figure 3:
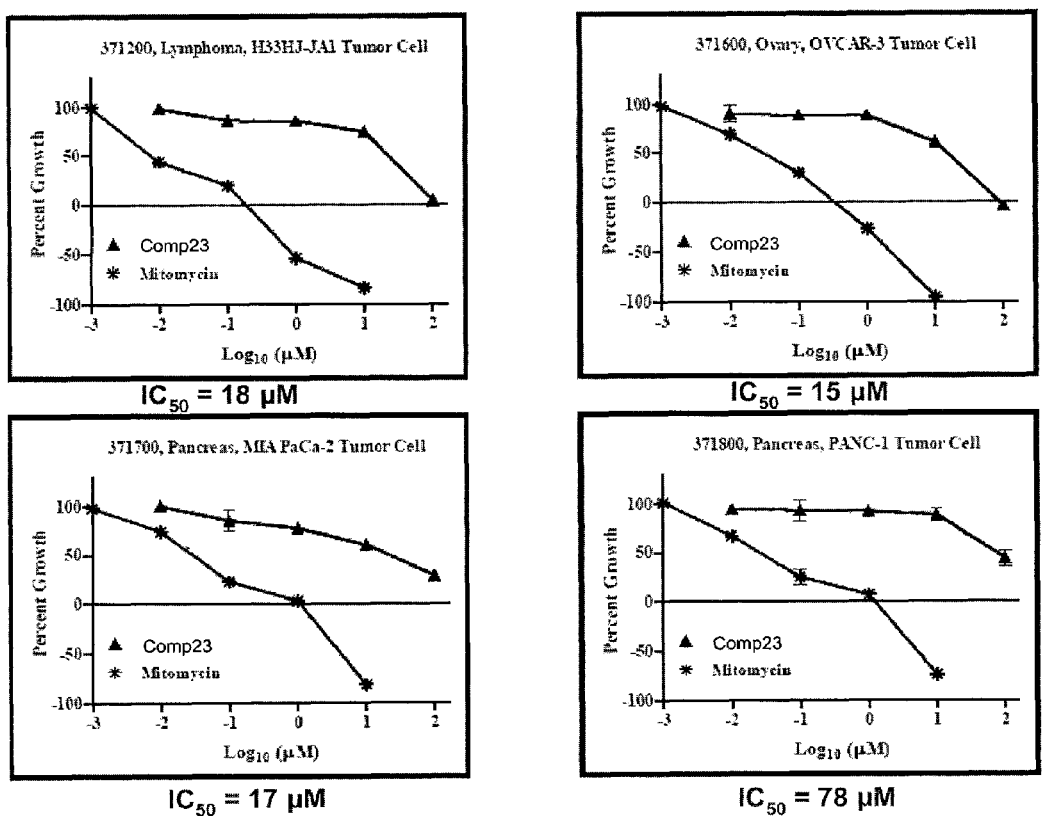
FIG. 3 is an illustrative panel of scatter plots showing the effect of the HDAC8-selective inhibitor compound, Compound 23, on cell proliferation in four cell lines.
Figure 4:
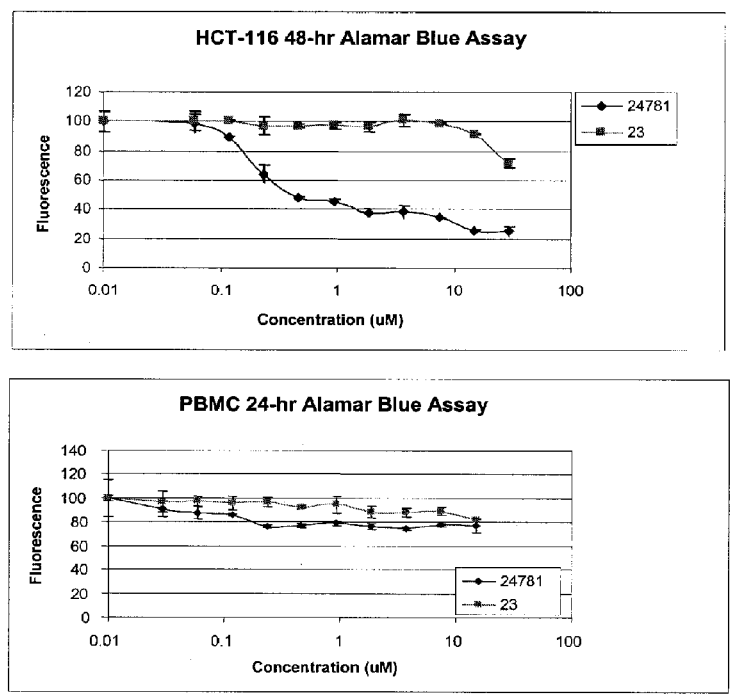
FIG. 4 is an illustrative panel of scatter plots showing the effect of the HDAC8-selective inhibitor compound, Compound 23, on cell proliferation in the cell line HCT116 and in normal human peripheral blood mononuclear cells.
Figure 5:
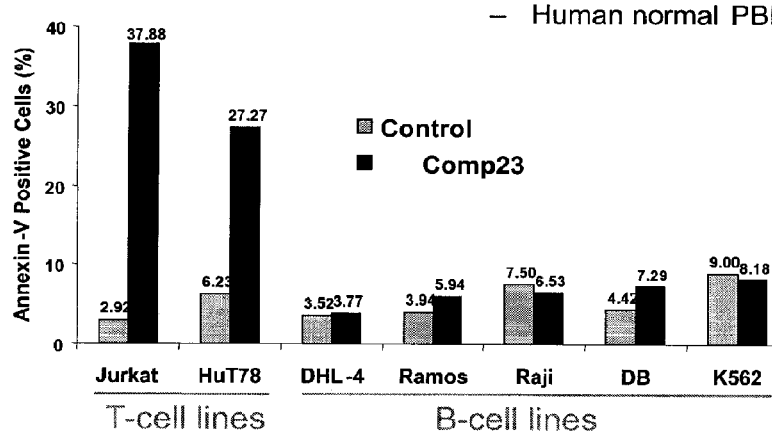
FIG. 5 is an illustrative scatter plot showing the effect of the HDAC8-selective inhibitor compound, Compound 23, on cell proliferation in T-cell-derived and B-cell-derived cell lines.

As shown in FIG. 3, Compound 23, was relatively ineffective for inhibiting the growth of any of the H33HJ-JA1 (lymphoma), the OVCAR-3 (ovary), MIA-PaCa-2 (pancreas), or PANC-1 (pancreas) tumor cell lines, especially as compared to the established anti-proliferative agent mitomycin. Likewise, Compound 23 failed to inhibit the growth of the HCT116 (human colon carcinoma) cell line or PBMCs (FIG. 4). In contrast, Compound 23 was cytotoxic to the Jurkat and HuT78 T-cell derived tumor cell lines, whereas the B-cell derived cell lines DB and Ramos were not affected (FIG. 5). Based on these data, we conclude that the selective HDAC8 inhibitor compound effectively and specifically inhibits proliferation of T-cell tumor-cells.

Example 4

Figure 6:
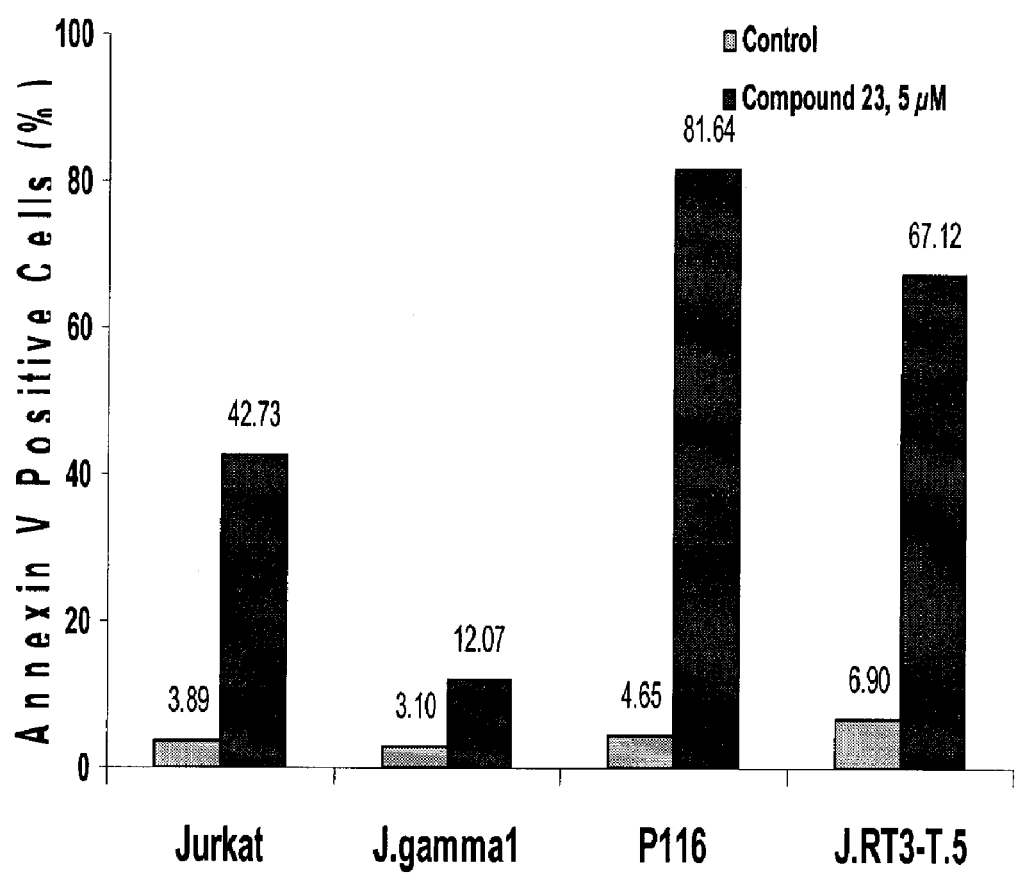
FIG. 6 is an illustrative bar graph showing the ability of an HDAC8 inhibitor compound (compound 23; 5 µM) to effect apoptosis in Jurkat cells that are wild-type (Jurkat); phospholipase C-γ1 deficient (J.gamma1); T-cell receptor-deficient (P116); or ZAP-70-deficient (JRT3-T.5). Jurkat cells are human T-cell leukemia established from the peripheral blood of a 14 year old boy with acute lymphoblastic leukemia.
Figure 9:
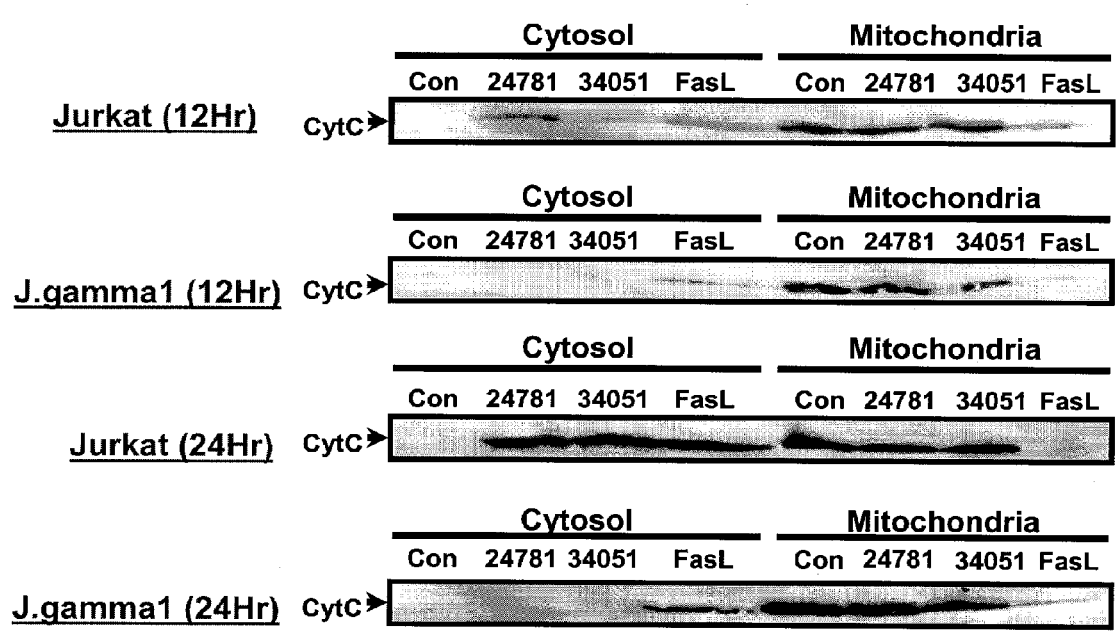
FIG. 9 is an illustrative series of immunoblot images demonstrating the translocation of cytochrome C oxidase translocation from mitochondria to cytosol in wild-type (Jurkat) versus J.γ1 (J.gamma1) Jurkat cells at various time points following treatment with pro-apoptotic agents.

HDAC Inhibitor Compound-Induced Apoptosis Requires Phospholipase C-γ1 (PLC-γ1) Signaling In order to further characterize the pro-apoptotic activity of Compound 23, we tested its effect on Jurkat cells deficient in various steps of the T-cell receptor (TCR) signaling pathway. As shown in FIG. 6, and Table 4, Compound 23 (5 µM), as well as a pan-HDAC inhibitor compound induced much less apoptosis in PLC-γ1-deficient Jurkat cells (J.γ1) than in wild type, TCR-deficient (J.RT3-T.5), or ZAP-70-deficient (P116) Jurkat cells.

we examined cytochrome C translocation from mitochondria to cytosol, a hallmark of apoptosis, in response to compound 23 or a pan-HDAC inhibitor compound. As shown in FIG. 9 treatment with Compound 23 or the pan-HDAC compound for 12 or 24 hours induced translocation of cytochrome oxidase from mitochondria to cytosol in wild type Jurkat cells. In contrast, the same treatments in the PLC-deficient J. cells, failed to alter the localization of cytochrome C. FasL, a pro-apoptotic protein, effectively induced translocation of cytochrome C in both WT and J.γ1 Jurkat cells.

Based on these results it was concluded that Compound 23, an HDAC8-selective inhibitor compound induces apoptosis in T-cell derived lymphoma cells through a pathway that is dependent on the PLC signaling pathway. This suggests that activating the PLC signaling pathway is a useful therapeutic approach for treatment of T-cell proliferative disorders. Thus, HDAC inhibitor compounds (e.g., HDAC8-selective inhibitor compounds) alone or in combination with agents that activate PLC-dependent signaling (e.g., receptor agonists, receptor-activating, antibodies, thapsigargin, etc.) can be used to treat T-cell proliferative disorders. Conversely, profiling the PLC-signaling characteristics (e.g., PLC mRNA or protein levels, PLC enzymatic activity, or PLC-dependent changes in intracellular calcium levels) may be useful for determining cells likely to be responsive to an HDAC8-selective inhibitor.

Example 5

HDAC Inhibitors Induce PLC-γ Dependent Intracellular Calcium Mobilization

Figure 10:
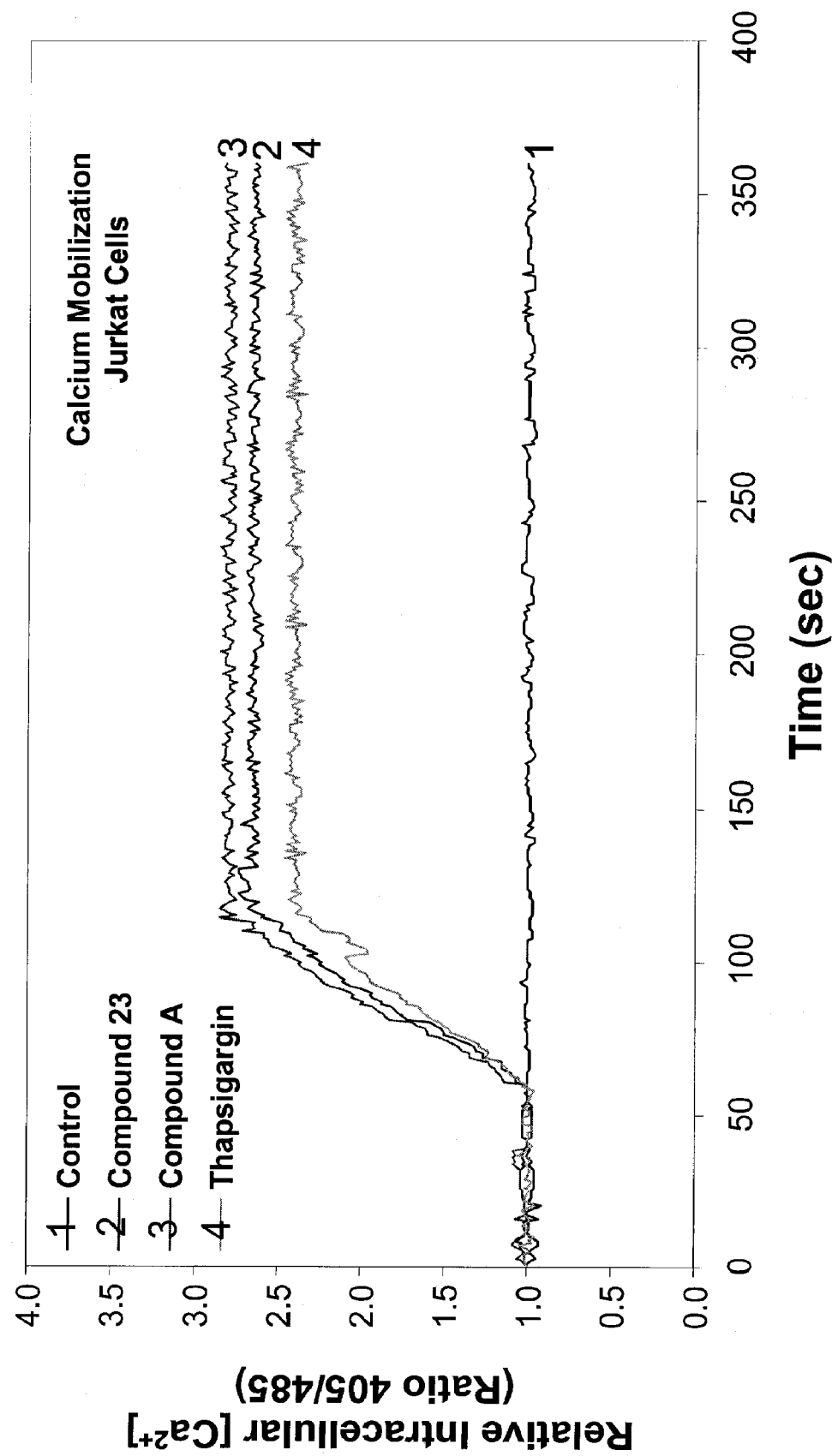
FIG. 10 is an illustrative line graph showing the time course plots of intracellular calcium mobilization in cultured Jurkat cells in response to an HDAC8-selective inhibitor compound (Compound 23), a pan-HDAC inhibitor compound (Compound A), thapsigargin (a calcium effector), or a vehicle control.

Ratiometric fluorescence calcium imaging was used to evaluate the effect of the HDAC-8 selective inhibitor compound, Compound 23, and CRA-024781 (a pan-HDAC inhibitor compound) on intracellular calcium mobilization in T-cell and B-cell-derived cell lines. As shown in FIG. 10, the addition of 10 µM compound 23 or CRA-024781 to cultured Jurkat cells, a T-cell derived cell line, resulted in a rapid

TABLE 4

Apoptosis in WT and signaling mutant Jurkat cells

| 3 Day dose T-Cell line | Compound 23 | | Pan-HDAC Inhibitor Compound | | Phenotype |
|---|---|---|---|---|---|
| | GI50 (µM) | Apoptosis at 5 µM (%) | GI50 (mM) | Apoptosis at 0.125 mM (%) | |
| Jurkat WT | 2.4 | 43 | 0.13 | 48 | Parent T-lymphocyte |
| J.g1 | 4.0 | 12 | 0.14 | 18 | Phospholipase C-g1 deficient |
| P116 | 10.2 | 82 | 0.19 | 76 | ZAP-70 deficient |
| J.RT3-T.5 | 5.1 | 67 | 0.14 | 32 | TCR-b chain deficient |

Figure 7:
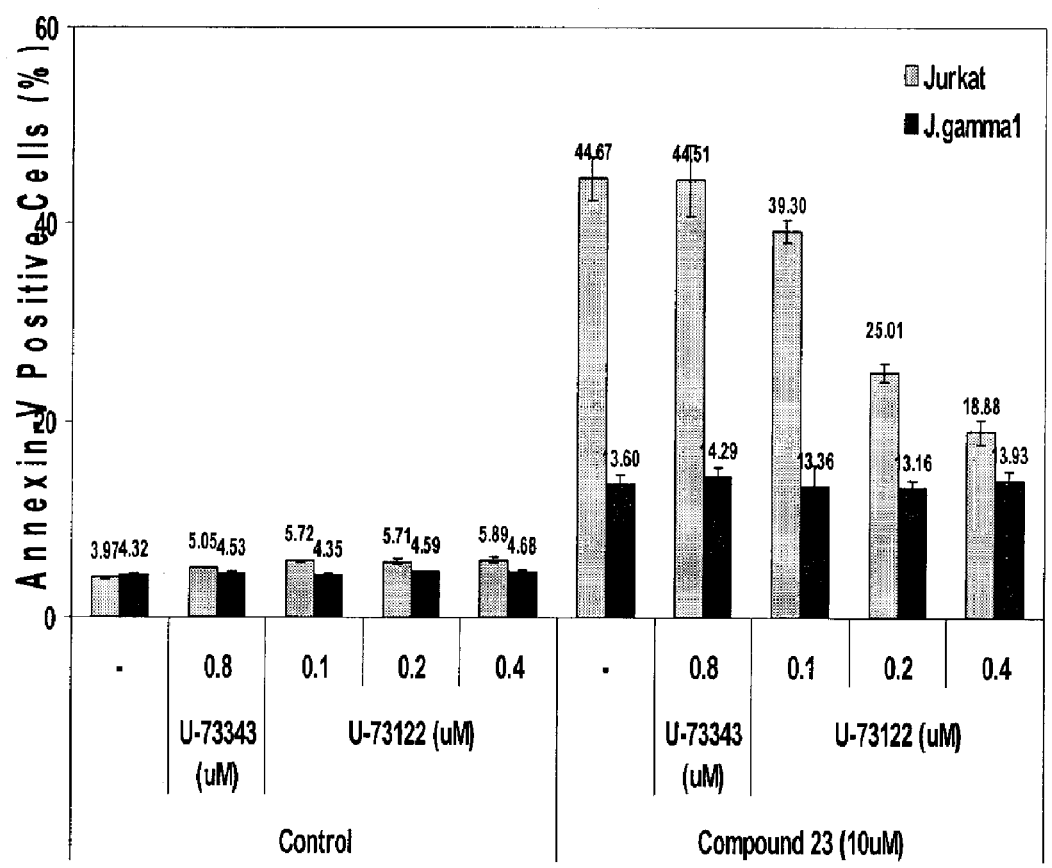
FIG. 7 is an illustrative bar graph showing the effect of a phospholipase C inhibitor on apoptosis induced by an HDAC8 inhibitor compound (compound 23; 10 µM) in wild-type (Jurkat) versus J.γ1 (J.gamma1) Jurkat cells.

This result suggested that PLC-γ1 signaling was necessary for the induction of apoptosis in T-cell lines by Compound 23. Indeed, as shown in FIG. 7, a PLC inhibitor (U-73122) inhibited Compound 23-induced apoptosis in a dose-dependent manner. In contrast, an inactive analog of the PLC inhibitor (U-73343) failed to block Compound 23-induced apoptosis.

Figure 11:
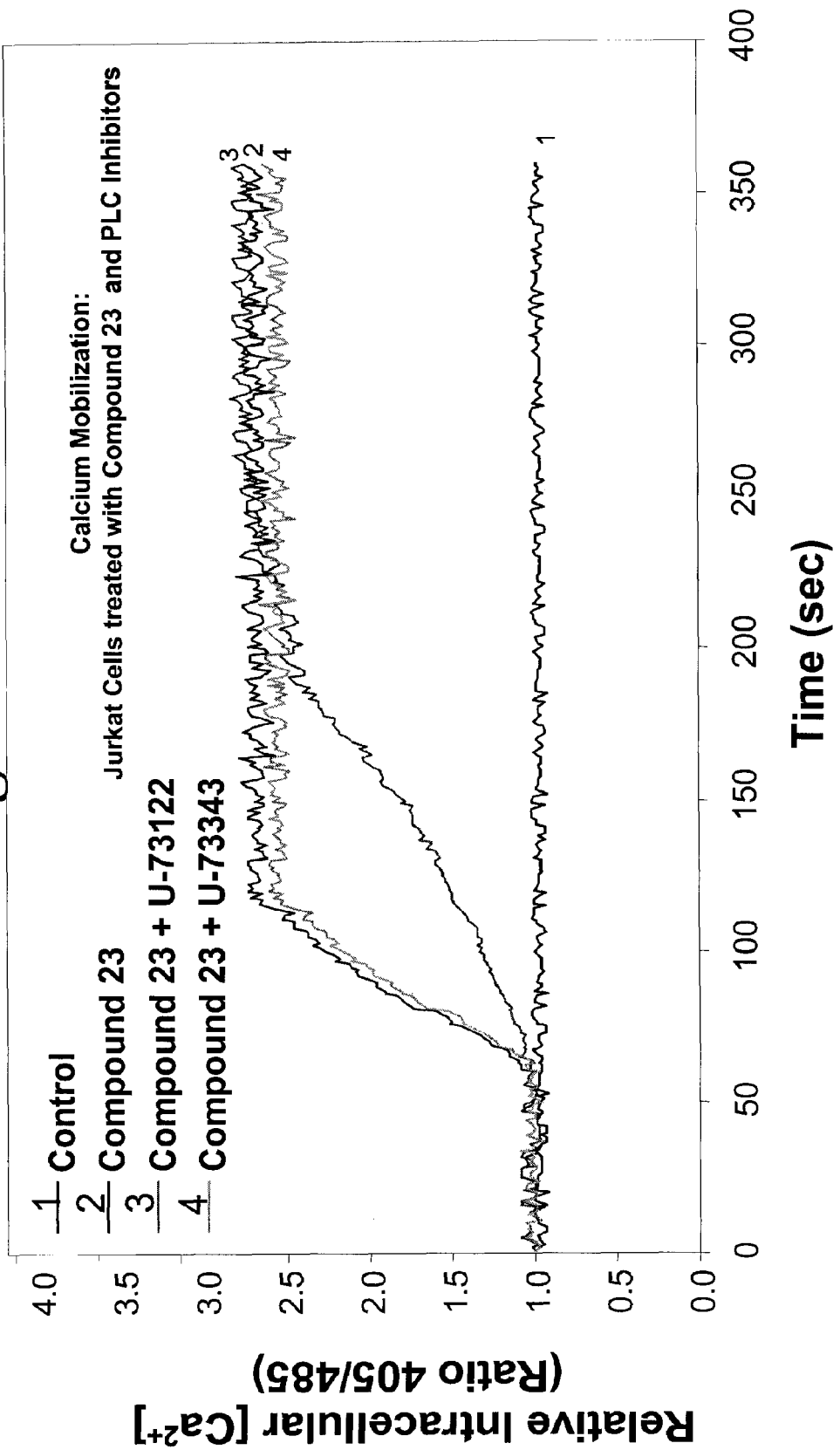
FIG. 11 is an illustrative line graph showing the time course plots of intracellular calcium mobilization in cultured Jurkat cells in response to an HDAC8-selective inhibitor compound (Compound 23) in the presence of a phospholipase C inhibitor compound (U-73122) or its inactive analog (U-73343).
Figure 12:
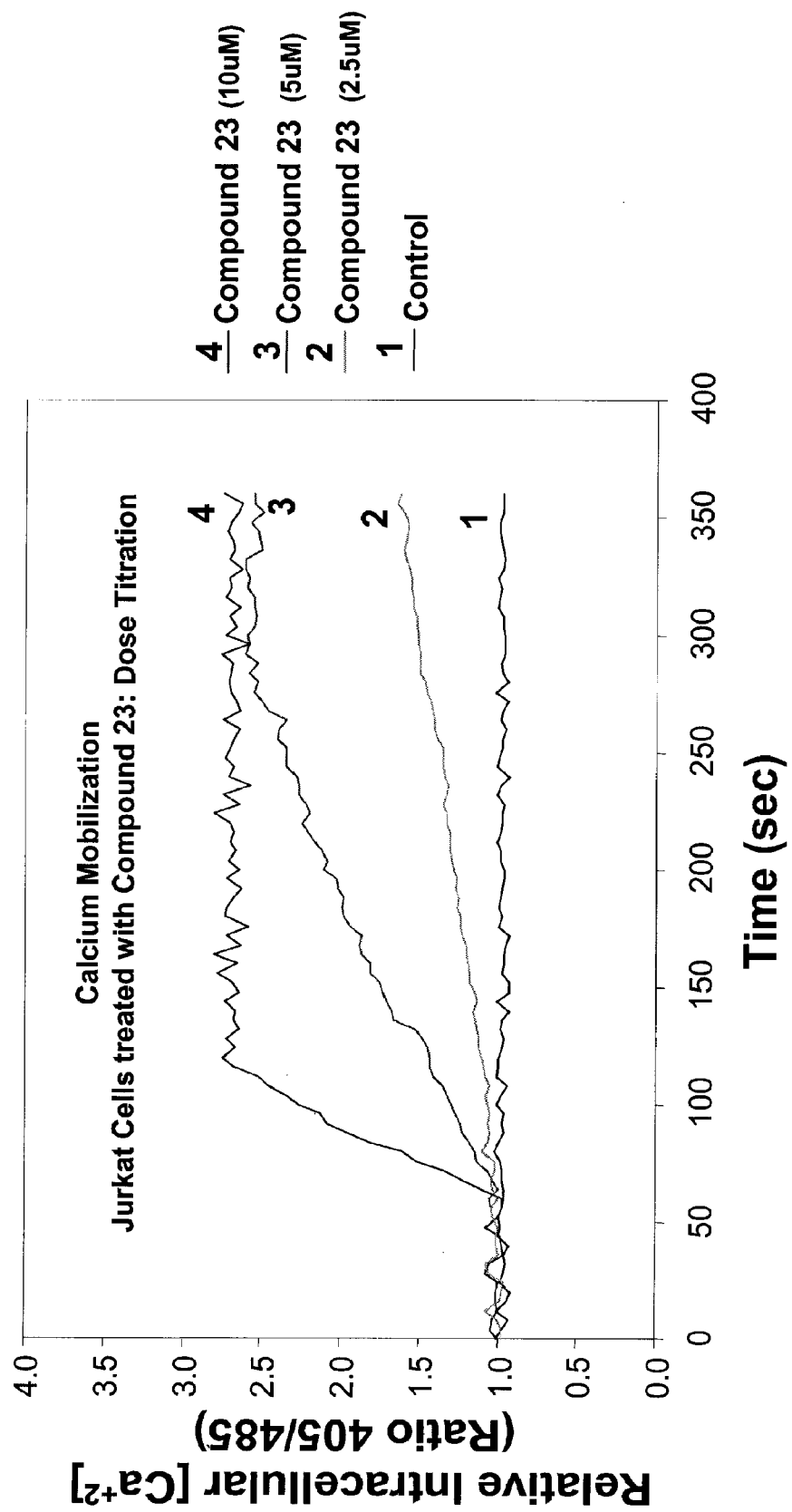
FIG. 12 is an illustrative line graph showing dose-dependent intracellular calcium responses induced by a HDAC8-selective inhibitor compound (Compound 23) in Jurkat cells.
Figure 13:
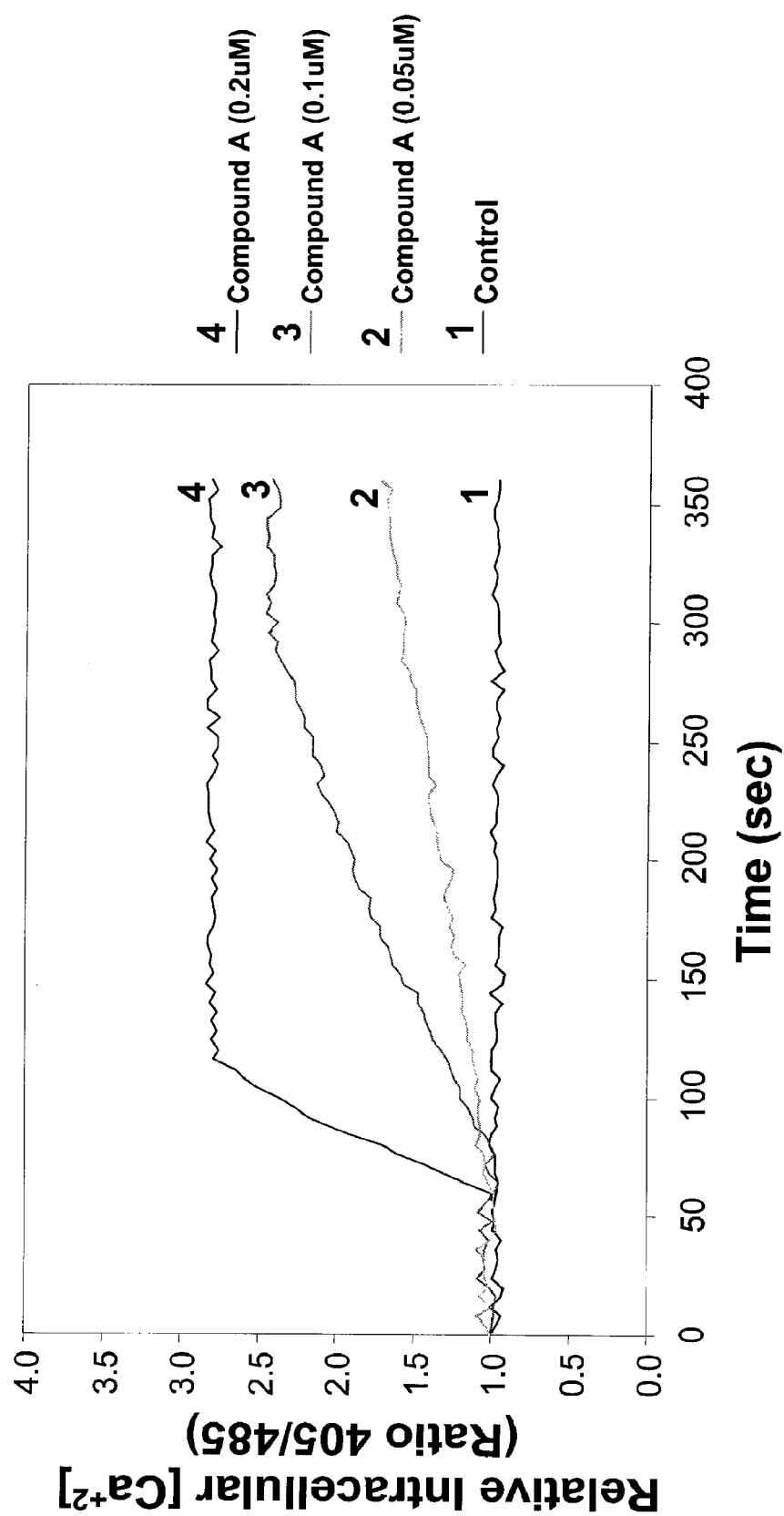
FIG. 13 is an illustrative line graph showing dose-dependent intracellular calcium responses induced by a pan-HDAC inhibitor compound (Compound A) in Jurkat cells.
Figure 14:
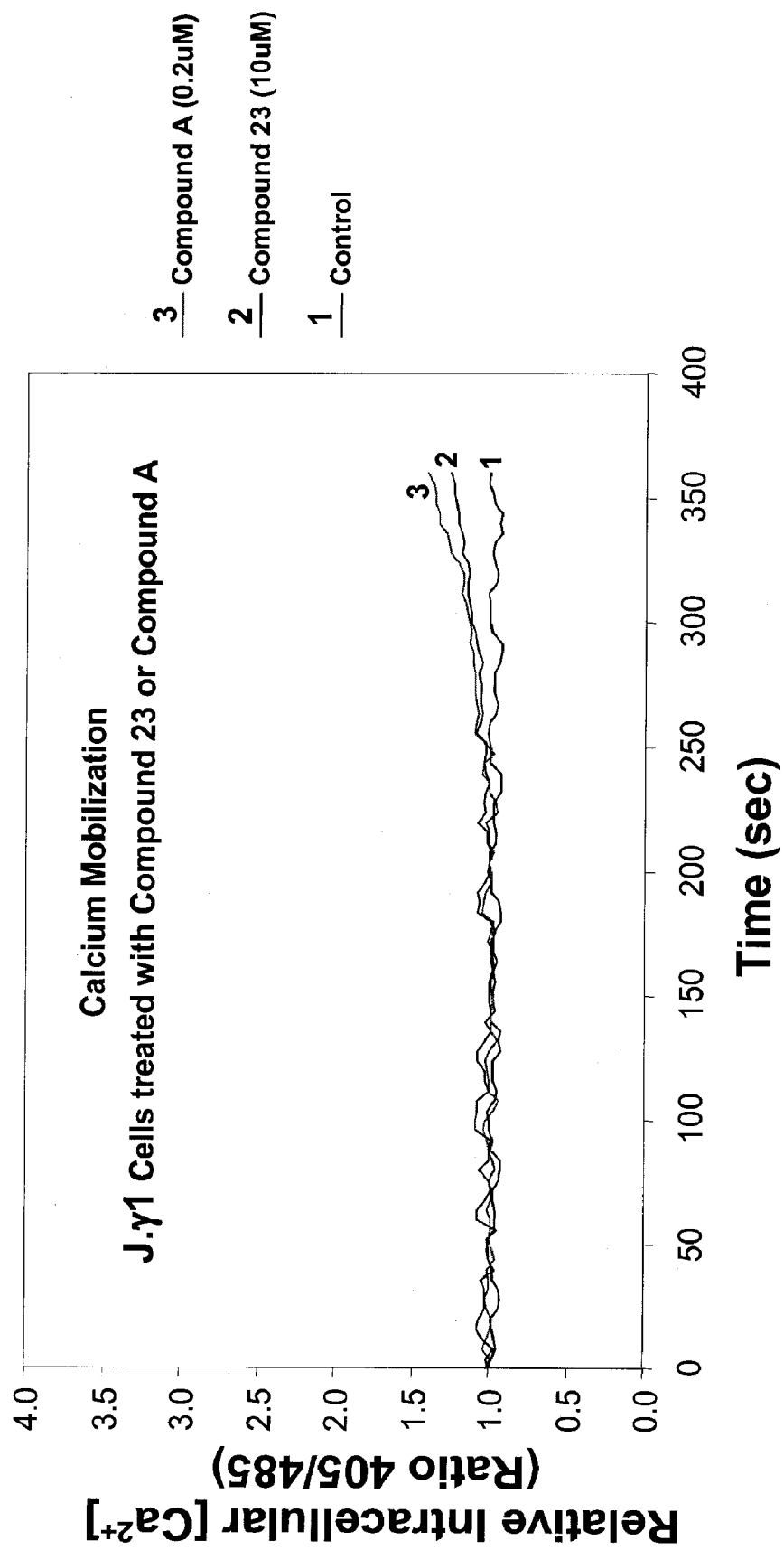
FIG. 14 is an illustrative line graph showing the time course plots of intracellular calcium mobilization in phospholipase C-γ1-deficient Jurkat cells in response to an HDAC8-selective inhibitor compound (Compound 23) or a pan-HDAC inhibitor compound (Compound A).
Figure 15:
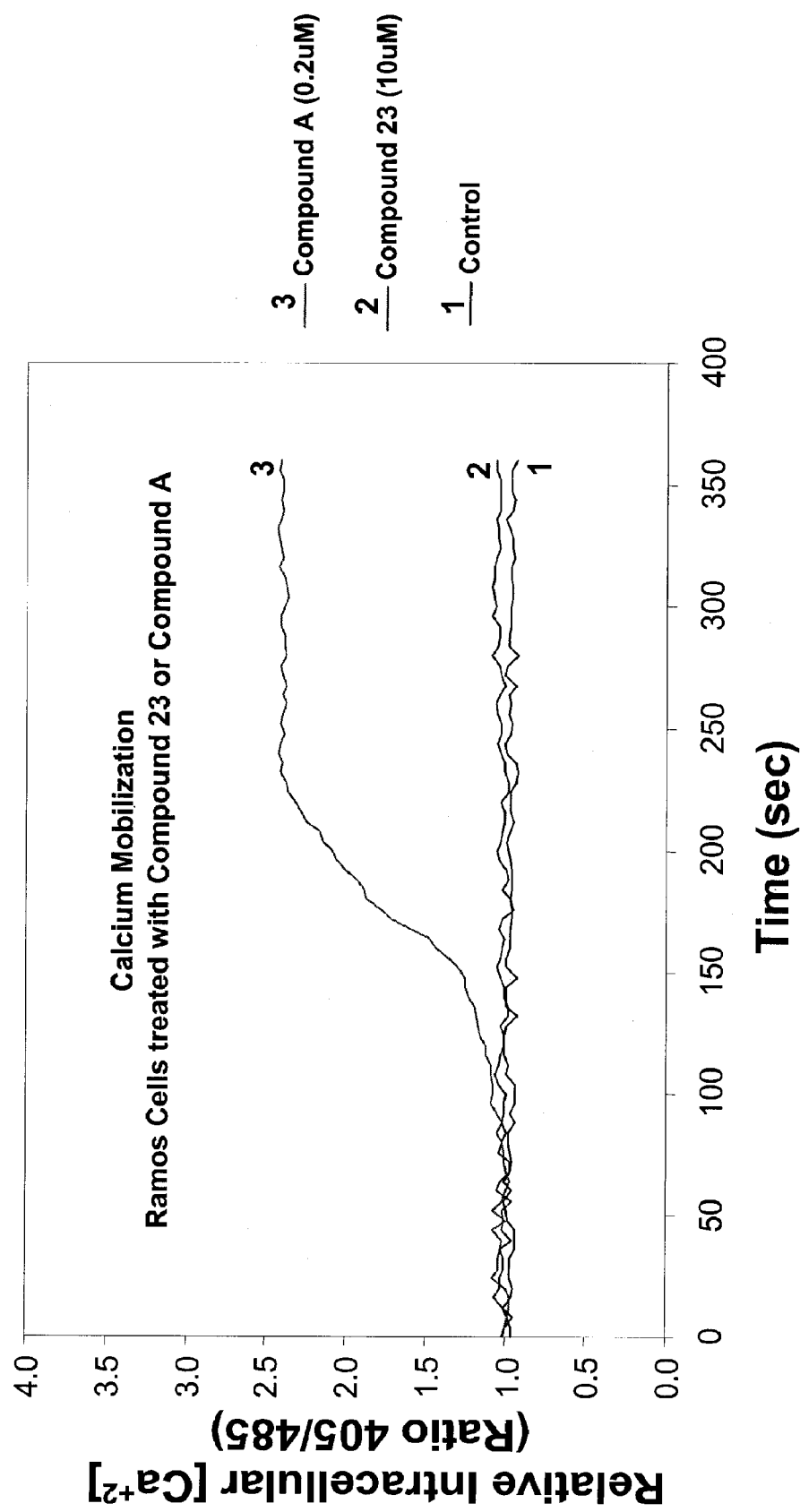
FIG. 15 is an illustrative graph showing the time course plots of intracellular calcium mobilization in cultured Ramos cells (derived from B-cells) in response to an HDAC8-selective inhibitor compound (Compound 23), a pan-HDAC inhibitor compound (Compound A), or a vehicle control.

Consistent with the role of PLC in Compound 23-induced apoptosis, we found that the Ca$^{2+}$-effector thapsigargin (0.2 µM) enhanced apoptosis, as shown in FIG. 8(A). In contrast, the Ca$^{2+}$-chelator, BAPTA-AM (0.5 µM) diminished apoptosis induced by Compound 23, as shown in FIG. 8(B). Finally, (approximately 1 minute) and sustained rise in intracellular calcium very similar to that observed for the Ca$^{2+}$-effector, thapsigargin (0.2 µM). As shown in FIG. 11, the compound 23-stimulated increase in intracellular Ca$^{2+}$ levels was strongly inhibited by the PLC inhibitor (U-73122), but not its inactive analog (U-73343), consistent with the effect of these compounds on apoptosis (Example 5). Further, the effect of either compound on intracellular Ca$^{2+}$ was completely abolished in PLC-γ1-deficient Jurkat J.γ1 cells (FIG. 14). Calcium mobilization by compound 23 and CRA-024781 in Jurkat cells was dose dependent, as shown in FIGS. 12 and 13, respectively. Interestingly, the HDAC8-selective compound 23 did not alter resting calcium levels in Ramos cells (FIG. 15), which are B-cell derived. This result was consistent this compound's failure to induce apoptosis in this cell line. In contrast, the PanHDACi compound induced a robust increase in intracellular calcium levels in this cell line (FIG. 15). Importantly, Ramos cells do not express PLC-γl.

Based on these data we concluded that compound 23 likely exerts its effects (calcium mobilization and apoptosis) on T-cell derived cells selectively by acting through a PLC-γ1-dependent pathway.

Example 6

Clinical Trial of HDAC8 Inhibitor in Patients with T-Cell Lymphomas

A clinical trial will be commenced to assess the effectiveness of a selective HDAC8 inhibitor in patients with T-cell lymphoma and who have failed at least one prior systemic therapy. It will be an interventional study that is non-randomized and open label. Patients will be administered doses of a composition containing a selective HDAC8 inhibitor. Subjects 18 years and older, both male and female, will be eligible for the study. Patients must have a histologically confirmed diagnosis of a T-cell lymphoma, and must have failed at least one line of prior systemic therapy. There is no limitation on the number of prior therapies. Patients must have had a chest x-ray, computed tomography (CT) scan or CT/positron emission tomography (PET) scan or severity-weighted assessment tool (SWAT) assessment within 3 weeks prior to enrollment and after completion of any prior cytotoxic chemotherapy. Patients with a history of bone marrow involvement must have had a bone marrow biopsy within 3 weeks of study enrollment. Patients must have adequate bone marrow and hepatic function, and an estimated life expectancy of greater than 3 months.

Patients must be free from other malignant diseases or be more than 5 years post-treatment completion for an invasive malignant disease. Patients with a known infection with HIV, hepatitis B or C must be excluded. Patients who have used any other investigational drugs within 4 weeks prior to study registration must also be excluded.

The objectives of the study are to determine the overall objective response rate of participants after 6 courses of treatment, the time to response, response duration, evaluate the safety and feasibility of the compound containing a selective HDAC8 inhibitor, and to determine the 2-year progression-free and overall survival rates.

Patients will receive a formulation containing a selective HDAC8 inhibitor at various dose schedules as required, with treatment repeated every 28 days for at least 6 courses in the absence of disease progression or unacceptable toxicity. Response will be assessed based on extent of disease remission.

Throughout the specification, claims and accompanying figures, a number of embodiments of the invention have been described. Nevertheless, it will be understood that various modifications may be made without departing from the spirit and scope of the invention. Accordingly, other embodiments are within the scope of the following claims.

What is claimed is:

1. A method for treating a T-cell proliferative disorder, comprising administering to a subject in need a composition containing a therapeutically effective amount of a selective inhibitor of histone deacetylase 8 activity.

2. The method of claim 1, wherein the selective inhibitor is a compound of formula Ia or IIa:

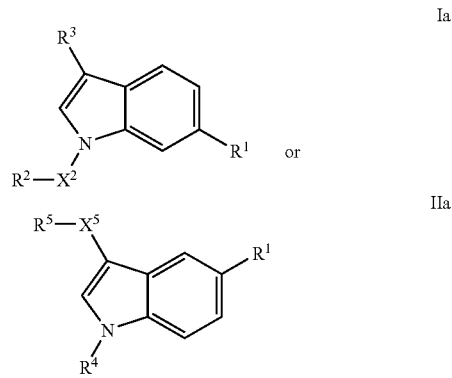

where $R^1$ in Formula Ia or IIa is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;

$R^3$ is hydrogen, alkyl, substituted alkyl, alkenyl, substituted alkenyl, hydroxy, alkoxy, or haloalkoxy;

$R^4$ is hydrogen, alkyl, substituted alkyl, alkenyl, substituted alkenyl, hydroxy, alkoxy, haloalkoxy, or optionally substituted phenyl;

$X^5$ is a bond, alkylene, or alkenylene where the alkylene or alkenylene is optionally substituted with halo; and $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

3. The method of claim 1, wherein the selective inhibitor is a compound of Formula Ib or IIb:

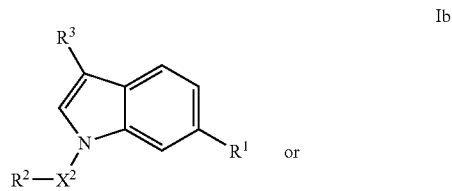

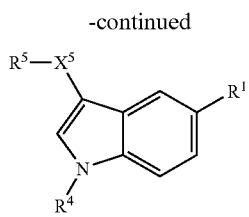

where

R¹ in Formula Ib or IIb is —C(O)NHOH;

X² is a bond, alkylene, or alkenylene where the alkylene or alkenylene is optionally substituted with one, two, three, four, or five halo;

R² is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

R³ is hydrogen, alkenyl, substituted alkenyl, hydroxy, alkoxy, haloalkoxy, or —X⁶—R⁶ where X⁶ is alkylene or alkenylene and X⁶ is additionally optionally substituted with one, two, three, four, of five halo; and R⁶ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)₀₋₂—, alkenyl-S(O)₀₋₂—, aminosulfonyl, alkylaminosulfonyl, dialkylaminosulfonyl, alkylsulfonyl-NRᶜ— (where Rᶜ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NRᵃRᵇ (where Rᵃ and Rᵇ are independently hydrogen, alkyl, substituted alkyl, alkenyl, alkynyl, substituted alkynyl, hydroxy, alkoxy, or alkenyloxy);

R⁴ is hydrogen, alkyl, substituted alkyl, alkenyl, substituted alkenyl, hydroxy, alkoxy, haloalkoxy, or optionally substituted phenyl; and X⁵ is a bond; and R⁵ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that R⁵ is not optionally substituted pyrrole or optionally substituted 2,5-dioxo-pyrrole; or X⁵ is alkylene or alkenylene where the alkylene or alkenylene is optionally substituted with halo; and R⁵ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

4. The method of claim 1, wherein the composition further comprises an agent that activates phospholipase C-gamma or induces intracellular calcium release.

5. The method of claim 1, wherein the composition is administered in combination with an additional agent effective against peripheral T cell lymphoma, lymphoblastic lymphoma, cutaneous T cell lymphoma, NK/T-cell lymphoma, adult T cell leukemia/lymphoma, T-cell acute lymphoblastic leukemia (T-ALL), T-cell chronic lymphoblastic leukemia (T-CLL), anaplastic large cell lymphoma, angioimmunoblastic T-cell lymphoma, enteropathy-type T-cell lymphoma, hepatosplenic T-cell lymphoma, mycosis fungoides/Sezary syndrome, or subcutaneous panniculitis-like T-cell lymphoma.

6. The method of claim 5, wherein the additional agent is a topical agent, antipruritic agent, mustard application, bone marrow transplant, stem cell transplant, surgery, phototherapy, chemotherapy, photochemotherapy, radiation therapy, immunotherapy, radioimmunotherapy, systemic therapy, or any combination thereof.

7. The method of claim 1, wherein (a) the number of proliferative T-cells in the subject decreases by at least 50%, and/or (b) the size, number and shape of tumors or plaques or patches on the skin of the subject decreases by at least 50% after administering the therapeutically effective amount of the selective inhibitor of histone deacetylase 8 activity.

8. The method of claim 1, wherein the subject is refractory or intolerant to at least one other treatment for a T-cell proliferative disorder.

9. The method of claim 1, further comprising administering to the subject a therapeutic agent to reduce side effects-nausea associated with the use of the composition.

10. The method of claim 1, wherein the daily dosage of the composition to the subject is about 0.02 to about 5000 mg.

11. A method for treating a T-cell proliferative disorder, comprising administering to a subject in need a plurality of autologous T-cells, wherein the T-cells are exposed ex vivo to a composition containing a selective inhibitor of histone deacetylase 8 activity at a concentration that is effective for selectively killing transformed T-cells.

12. The method of claim 11, wherein the plurality of autologous T-cells is administered in combination with a composition containing a selective inhibitor of histone deacetylase 8 activity.

13. The method of claim 11, wherein the selective inhibitor is a compound of formula Ia or IIa:

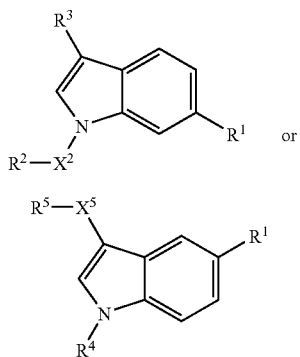

where
R¹ in Formula Ia or IIa is —C(O)NHOH;
X² is a bond, alkylene, or alkenylene where the alkylene or alkenylene is optionally substituted with one, two, three, four, or five halo;
R² is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;
R³ is hydrogen, alkyl, substituted alkyl, alkenyl, substituted alkenyl, hydroxy, alkoxy, or haloalkoxy;
R⁴ is hydrogen, alkyl, substituted alkyl, alkenyl, substituted alkenyl, hydroxy, alkoxy, haloalkoxy, or optionally substituted phenyl;
X⁵ is a bond, alkylene, or alkenylene where the alkylene or alkenylene is optionally substituted with halo; and
R⁵ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

14. The method of claim 11, wherein the selective inhibitor is a compound of Formula Ib or IIb:

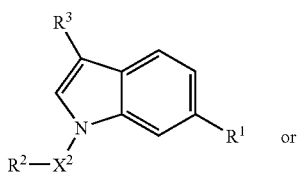

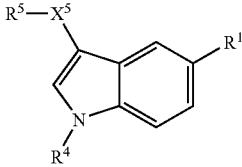

where
R¹ in Formula Ib or IIb is —C(O)NHOH;
X² is a bond, alkylene, or alkenylene where the alkylene or alkenylene is optionally substituted with one, two, three, four, or five halo;
R² is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;
R³ is hydrogen, alkenyl, substituted alkenyl, hydroxy, alkoxy, haloalkoxy, or —X⁶—R⁶ where X⁶ is alkylene or alkenylene and X⁶ is additionally optionally substituted with one, two, three, four, of five halo; and R⁶ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S (O)₀₋₂—, alkenyl-S(O)₀₋₂—, aminosulfonyl, alkylaminosulfonyl, dialkylaminosulfonyl, alkylsulfonyl-NRᶜ— (where Rᶜ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NRᵃRᵇ (where Rᵃ and Rᵇ are independently hydrogen, alkyl, substituted alkyl, alkenyl, alkynyl, substituted alkynyl, hydroxy, alkoxy, or alkenyloxy);
R⁴ is hydrogen, alkyl, substituted alkyl, alkenyl, substituted alkenyl, hydroxy, alkoxy, haloalkoxy, or optionally substituted phenyl; and
X⁵ is a bond; and R⁵ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

15. The method of claim 11, wherein the plurality of autologous T-cells is administered in combination with at least one additional agent effective against peripheral T cell lymphoma, lymphoblastic lymphoma, cutaneous T cell lymphoma, NK/T-cell lymphoma, adult T cell leukemia/lymphoma, T-cell acute lymphoblastic leukemia (T-ALL), T-cell chronic lymphoblastic leukemia (T-CLL), anaplastic large cell lymphoma, angioimmunoblastic T-cell lymphoma, enteropathy-type T-cell lymphoma, hepatosplenic T-cell lymphoma, mycosis fungoides/Sezary syndrome, or subcutaneous panniculitis-like T-cell lymphoma.

16. The method of claim 15, wherein the agent is a topical agent, antipruritic agent, mustard application, bone marrow transplant, stem cell transplant, surgery, phototherapy, chemotherapy, photochemotherapy, radiation therapy, immunotherapy, radioimmunotherapy, systemic therapy, or any combination thereof.

17. A method for predicting responsiveness to a treatment for a T-cell proliferative disorder, comprising: determining the level of histone deacetylase 8 activity in a biological sample from a subject having the T-cell proliferative disorder, and providing information that a higher level of the histone deacetylase 8 activity is indicative of the subject's higher likelihood of responsiveness to a composition containing a selective inhibitor of histone deacetylase 8 activity.

18. The method of claim 17, wherein the selective inhibitor is a compound of formula Ia or IIa:

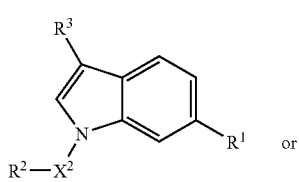

Ia

-continued

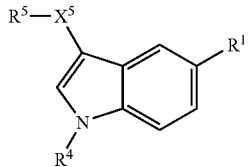

IIa where $R^1$ in Formula Ia or IIa is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;

$R^3$ is hydrogen, alkyl, substituted alkyl, alkenyl, substituted alkenyl, hydroxy, alkoxy, or haloalkoxy;

$R^4$ is hydrogen, alkyl, substituted alkyl, alkenyl, substituted alkenyl, hydroxy, alkoxy, haloalkoxy, or optionally substituted phenyl;

$X^5$ is a bond, alkylene, or alkenylene where the alkylene or alkenylene is optionally substituted with halo; and $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

19. The method of claim 17, wherein the selective inhibitor is a compound of Formula Ib or IIb:

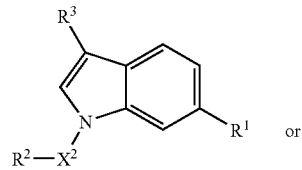

Ib or

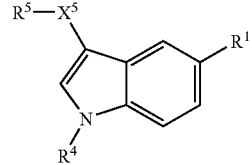

IIb where $R^1$ in Formula Ib or IIb is —C(O)NHOH;

$X^2$ is a bond, alkylene, or alkenylene where the alkylene or alkenylene is optionally substituted with one, two, three, four, or five halo;

R² is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

R³ is hydrogen, alkenyl, substituted alkenyl, hydroxy, alkoxy, haloalkoxy, or —X⁶—R⁶ where X⁶ is alkylene or alkenylene and X⁶ is additionally optionally substituted with one, two, three, four, of five halo; and R⁶ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-S(O)₀₋₂—, alkenyl-S(O)₀₋₂—, aminosulfonyl, alkylaminosulfonyl, dialkylaminosulfonyl, alkylsulfonyl-NR$^c$— (where R$^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)NR$^a$R$^b$ (where R$^a$ and R$^b$ are independently hydrogen, alkyl, substituted alkyl, alkenyl, alkynyl, substituted alkynyl, hydroxy, alkoxy, or alkenyloxy);

R⁴ is hydrogen, alkyl, substituted alkyl, alkenyl, substituted alkenyl, hydroxy, alkoxy, haloalkoxy, or optionally substituted phenyl; and X⁵ is a bond; and R⁵ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that R⁵ is not optionally substituted pyrrole or optionally substituted 2,5-dioxo-pyrrole; or X⁵ is alkylene or alkenylene where the alkylene or alkenylene is optionally substituted with halo; and R⁵ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

20. The method of claim 17, wherein the level of histone deacetylase 8 activity is determined by measuring the level of phospholipase C-gamma activity, mRNA, protein, or phospholipase C-gamma dependent changes in intracellular calcium levels.

21. The method of claim 20, wherein the composition further comprises an agent that activates phospholipase C-gamma or induces intracellular calcium release.

22. A method for predicting efficacy of a treatment for a T-cell proliferative disorder comprising: administering to a subject having a T-cell proliferative disorder a composition containing a selective inhibitor of histone deacetylase 8 activity; monitoring the subject's histone deacetylase 8 activity for an increase or decrease in activity; and utilizing the patient's histone deacetylase 8 activity as an indication for the amount of the next dosage of the compound.

23. The method of claim 22, wherein the selective inhibitor is a compound of formula Ia or IIa:

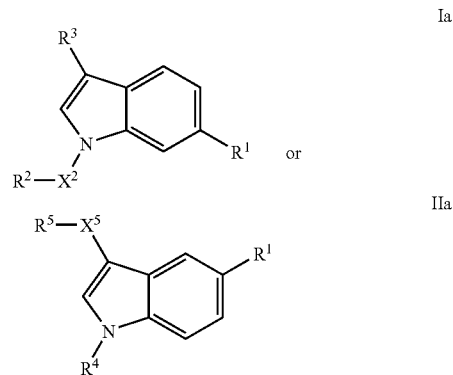

where

R¹ in Formula Ia or IIa is —C(O)NHOH;

X² is a bond, alkylene, or alkenylene where the alkylene or alkenylene is optionally substituted with one, two, three, four, or five halo;

R² is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro;

R³ is hydrogen, alkyl, substituted alkyl, alkenyl, substituted alkenyl, hydroxy, alkoxy, or haloalkoxy;

R⁴ is hydrogen, alkyl, substituted alkyl, alkenyl, substituted alkenyl, hydroxy, alkoxy, haloalkoxy, or optionally substituted phenyl;

$X^5$ is a bond, alkylene, or alkenylene where the alkylene or alkenylene is optionally substituted with halo; and $R^5$ is aryl, cycloalkyl, heteroaryl, or heterocycloalkyl where the aryl, cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

24. The method of claim 22, further comprising adjusting the dosage of the composition administered to the subject.

25. The method of claim 22, wherein the selective inhibitor is a compound of Formula Ib or IIb:

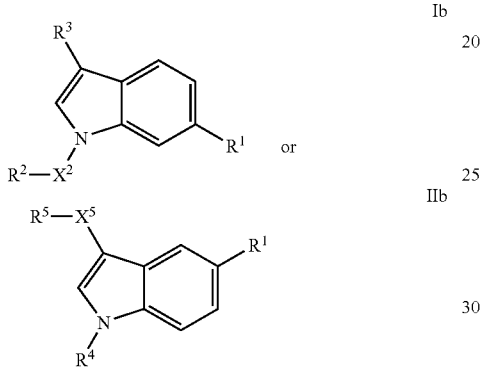

where $R^1$ in Formula Ib or IIb is —C(O)NHOH;

$X^2$ is a bond, alkylene, or alkenylene where the alkylene or alkenylene is optionally substituted with one, two, three, four, or five halo;

$R^2$ is aryl, cycloalkyl, heteroaryl, or heterocycloalkyl where the aryl is substituted with one, two, or three acyloxy, alkyl, substituted alkyl, alkenyl, substituted alkenyl, alkylamino, dialkylamino, or haloalkoxy; where the cycloalkyl is optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, halo, haloalkoxy, or nitro; and where the heteroaryl and the heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, carboxy, cyano, haloalkoxy, or nitro;

$R^3$ is hydrogen, alkenyl, substituted alkenyl, hydroxy, alkoxy, haloalkoxy, or —$X^6$—$R^6$ where $X^6$ is alkylene or alkenylene and $X^6$ is additionally optionally substituted with one, two, three, four, of five halo; and $R^6$ is alkylcarbonyl, alkenylcarbonyl, optionally substituted cycloalkylcarbonyl, alkylcarbonyloxy, alkenylcarbonyloxy, amino, alkylamino, dialkylamino, cyano, cyanoalkylaminocarbonyl, alkoxy, alkenyloxy, hydroxyalkoxy, halo, alkylcarbonylamino, alkyl-$S(O)_{0-2}$—, alkenyl-$S(O)_{0-2}$—, aminosulfonyl, alkylaminosulfonyl, dialkylaminosulfonyl, alkylsulfonyl-$NR^c$— (where $R^c$ is hydrogen, alkyl, substituted alkyl, alkenyl, substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonylamino, alkylaminocarbonylamino, dialkylaminocarbonylamino, alkoxyalkyloxy, or —C(O)$NR^aR^b$ (where $R^a$ and $R^b$ are independently hydrogen, alkyl, substituted alkyl, alkenyl, alkynyl, substituted alkynyl, hydroxy, alkoxy, or alkenyloxy);

$R^4$ is hydrogen, alkyl, substituted alkyl, alkenyl, substituted alkenyl, hydroxy, alkoxy, haloalkoxy, or optionally substituted phenyl; and $X^5$ is a bond; and $R^5$ is phenyl, 3- to 8-membered monocyclic cycloalkyl, 5- or 6-membered monocyclic heteroaryl, or 3- to 8-membered monocyclic heterocycloalkyl where the 3- to 8-membered monocyclic cycloalkyl, 5- or 6-membered monocyclic heteroaryl, and 3- to 8-membered monocyclic heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the phenyl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; provided that $R^5$ is not optionally substituted pyrrole or optionally substituted 2,5-dioxo-pyrrole; or $X^5$ is alkylene or alkenylene where the alkylene or alkenylene is optionally substituted with halo; and $R^5$ is aryl, cycloalkyl, heteroaryl, or heterocycloalkyl where the cycloalkyl, heteroaryl, and heterocycloalkyl are optionally substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; and the aryl is substituted with one, two, or three acyl, acylamino, acyloxy, alkyl, substituted alkyl, alkenyl, substituted alkenyl, alkoxy, alkoxycarbonyl, amino, alkylamino, dialkylamino, alkylaminocarbonyl, dialkylaminocarbonyl, optionally substituted arylaminocarbonyl, optionally substituted heteroarylaminocarbonyl, carboxy, cyano, halo, haloalkoxy, or nitro; or a pharmaceutically acceptable salt thereof.

26. The method of claim 22, wherein the monitoring of the subject's histone deacetylase 8 activity comprises measuring the subject's phospholipase C activity, mRNA, protein level, or phospholipase C dependent changes in intracellular calcium levels.

27. The method of claim 22, wherein the composition further contains an agent that activates phospholipase C or induces intracellular calcium release.

* * * * *